(12) United States Patent
Sato et al.

(10) Patent No.: US 8,684,995 B2
(45) Date of Patent: Apr. 1, 2014

(54) TREATMENT METHOD

(75) Inventors: Masatoshi Sato, Yokohama (JP); Kunihide Kaji, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 574 days.

(21) Appl. No.: 12/170,778

(22) Filed: Jul. 10, 2008

(65) Prior Publication Data
US 2010/0010293 A1    Jan. 14, 2010

(51) Int. Cl.
  A61M 31/00    (2006.01)
  A61B 1/00     (2006.01)
  A61B 17/10    (2006.01)
  A61B 17/08    (2006.01)
  A61B 17/34    (2006.01)

(52) U.S. Cl.
  USPC ........... 604/500; 600/101; 600/104; 606/142; 606/151; 606/153; 606/157; 606/185

(58) Field of Classification Search
  USPC ......... 623/23.64, 23.65–23.67; 606/151–156, 606/185–189, 213–221
  See application file for complete search history.

(56) References Cited

U.S. PATENT DOCUMENTS

| | | | | |
|---|---|---|---|---|
| 4,997,435 A | * | 3/1991 | Demeter | 606/127 |
| 5,441,507 A | * | 8/1995 | Wilk | 606/139 |
| 5,536,248 A | * | 7/1996 | Weaver et al. | 604/506 |
| 2005/0143763 A1 | * | 6/2005 | Ortiz et al. | 606/153 |
| 2008/0208161 A1 | | 8/2008 | Kaji et al. | |

FOREIGN PATENT DOCUMENTS

| | | |
|---|---|---|
| JP | 2005-193044 | 7/2005 |
| WO | WO 02/19923 A1 | 3/2002 |

* cited by examiner

*Primary Examiner* — Andrew Iwamaye
*Assistant Examiner* — Leslie Coburn
(74) *Attorney, Agent, or Firm* — Scully, Scott, Murphy & Presser, P.C.

(57) ABSTRACT

A treatment method on tissues in a body cavity includes: a first step of forming a hole for communicating first body tissue with second body tissue while both are in close contact with each other; and a second step of endoscopically inserting a treatment device into the second body tissue through the hole.

17 Claims, 44 Drawing Sheets

TREATMENT METHOD

BACKGROUND OF THE INVENTION

1. Field of the Invention

The present invention relates to a treatment method, and more particularly to a treatment method on tissues in a body cavity by using a tissue fastener for closely fixing two tissues together.

2. Description of Related Art

As a technique for performing a treatment on a human organ or the like, there is known laparoscopic surgery in which a treatment device is percutaneously inserted. This requires less invasion than the case of making an incision in an abdominal region. Therefore, an early recovery can be expected.

A treatment device for use in laparoscopic surgery has a hard shaft which is percutaneously inserted into a body. At a tip end of the shaft, there is provided forceps or the like. For example, Japanese Unexamined Patent Publication, First Publication No 2005-193044 discloses a treatment device for use in application for joining hollow organs. In this intraluminal anastomosis apparatus, a grip device which is freely opened/closed is attached to the tip end of the shaft. Into the shaft, there is inserted a fastener. The fastener is capable of being pushed out from the tip end of the shaft with a push-out mechanism on the proximal side. The fastener is manufactured by heat-treating a shape-memory alloy in a flat coil shape. It is inserted into the shaft in an extended state. In application, the fastener is pushed out with the push-out mechanism and piercingly inserted into a body. The fastener is heated by a body temperature and is restored into its original coil shape. Hollow organs are joined by the restored fastener.

Another example of providing a fastener is disclosed in PCT International Patent Publication No. WO 2002/019923. Here, a fastener is pushed out from a needle and is provided to tissue. Therefore, there are provided a stopper for controlling the amount of depth to which the needle is piercingly inserted into tissue and/or the amount of the fastener to be supplied to the tissue. When a treatment is performed, a device containing the fastener and the needle is placed against the tissue. When the needle is moved forward and piercingly inserted into the tissue, the position of the fastener is fixed with the stopper. After this, the needle is withdrawn from the tissue. The fastener does not move due to the presence of the stopper Therefore, a tip end portion of the fastener is left inside the tissue. When the device is detached from the tissue, the remaining part of the fastener is left outside the tissue. When the fastener assumes its original coil shape, the tissue is clamped.

SUMMARY OF THE INVENTION

The present invention is a treatment method on tissues in a body cavity, including: a first step of forming a hole for communicating first body tissue with second body tissue while both are in close contact with each other; and a second step of endoscopically inserting a treatment device into the second body tissue through the hole.

DETAILED DESCRIPTION OF THE INVENTION

Figure 1:
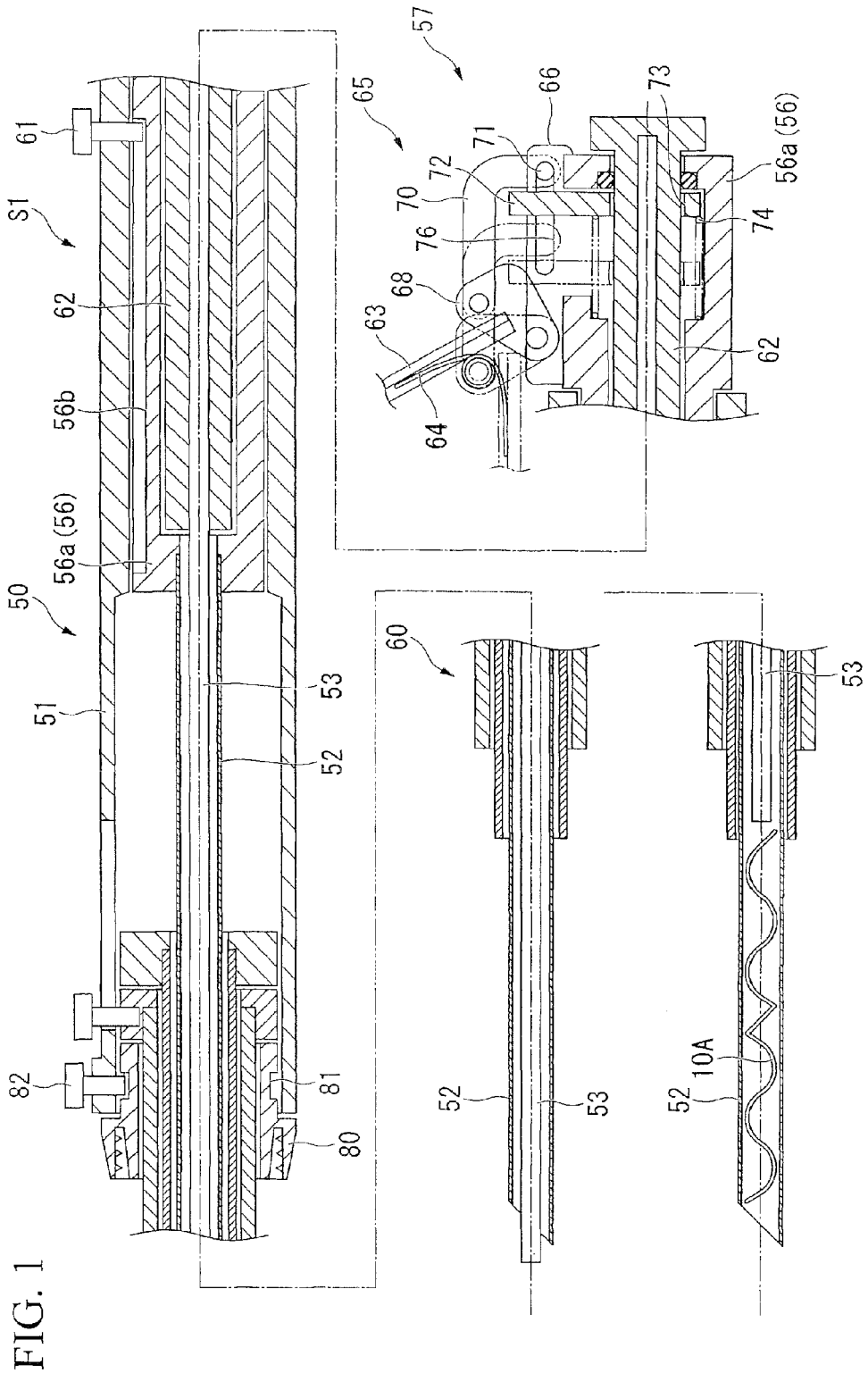
FIG. 1 is a cross-sectional view showing one example of a tissue fastening apparatus for use in a treatment method of the present invention.

A first embodiment of the present invention will be described. FIG. 1 shows one example of a tissue fastening apparatus for use in a treatment method of the present invention. As shown in FIG. 1, a tissue fastening apparatus S1 is an apparatus for performing a treatment of closely fixing first body tissue (hereinafter, referred to as "first tissue") and second body tissue (hereinafter, referred to as "second tissue") together to communicate both pieces of tissue. It includes: a tissue fastener (hereinafter, referred to simply as a "fastener") 10A; and an applicator 50. Note that the first tissue and the second tissue do not necessarily refer to different organs. For example, a given region of a given organ may be taken as a first tissue and another region of the same organ may be taken as second tissue, and these two regions may be fixed together.

Figure 2:
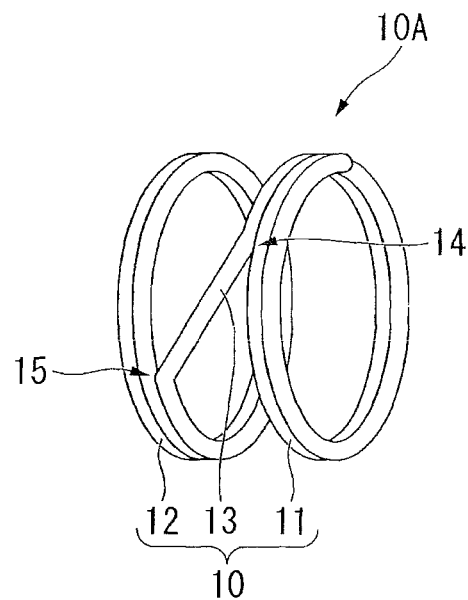
FIG. 2 is a perspective view showing a tissue fastener that makes up the tissue fastening apparatus.

The fastener 10A is a device for clamping the first tissue and the second tissue. It includes: a first fixation portion 11 that is locked on the first tissue; and a second fixation portion 12 that is locked on the second tissue, as shown in FIG. 2. Furthermore, the fastener 10A includes a linking portion 13 between the first fixation portion 11 and the second fixation portion 12 for linking the two.

Figure 3:
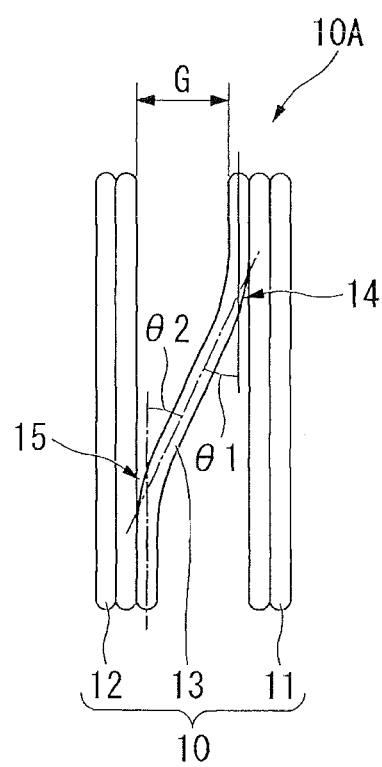
FIG. 3 is a plan view of the tissue fastener, seen from a different direction than in FIG. 2.

The fastener 10A is made of a string of highly-elastic, metal wire 10 in which all the portions thereof, that is, the first fixation portion 11, the second fixation portion 12, and the linking portion 13 are wound in a coil. In a part of the wire positioned between the first fixation portion 11 and the linking portion 13, there is formed a bent portion 14. In a part of the wire positioned between the linking portion 13 and the second fixation portion 12, there is similarly formed a bent portion 15. The first fixation portion 11 and the second fixation portion 12 form coils with the same diameter. With the provision of the linking portion 13, there is formed a gap G between them, as shown in FIG. 3. The central axis of the coil shape of the first fixation portion 11 coincides with that of the coil shape of the second fixation portion 12. As shown in FIG. 3, a wire portion forming the linking portion 13 has, at the bent portion 14, an angle θ1 with respect to a wire portion forming the coil of the first fixation portion 11. It also has, at the bent portion 15, an angle θ2 with respect to a wire portion forming the coil of the second fixation portion 12. The angle θ1 at the bent portion 14 is substantially the same as the angle θ2 at the bent portion 15 in degrees.

After the fastener 10A is extended, one end thereof is inserted into body tissue. Then, one fixation portion, for example the second fixation portion 12, is penetrated through the first tissue and the second tissue in this order. Restraint of the second fixation portion 12, which has been penetrated through the first tissue and the second tissue, is released on the second tissue side such that the second fixation portion 12 assumes its original coil shape and is locked on the second tissue. On the other hand, restraint of the first fixation portion 11 is released on the first tissue side such that the first fixation portion 11 assumes its original coil shape and is locked on the first tissue. With the first fixation portion 11 locked on the first tissue and the second fixation portion 12 locked on the second tissue, the first tissue and the second tissue are closely clamped so as to be pressed against each other. The linking portion 13 is left in the interiors of the clamped first tissue and second tissue.

The applicator 50 is a device for performing a treatment of leaving the fastener 10A within a body. It includes: an applicator main unit 51; a piercing device 52; and a stylet (a fastener pusher) 53, as shown in FIG. 1. The applicator main unit 51 is of a cylindrical shape. The piercing device 52 is of a needle tube shape. It is used with the fastener 10A being inserted therewithin. Note that electrodes may be provided at a tip end of the piercing device 52 and that the piercing device 52 may be piercingly inserted into the first tissue and the second tissue while burning the body tissue. In this case, the tip end of the piercing device 52 is not required to be sharp.

The stylet 53 is of a shaft-like shape. It is movably inserted inside the piercing device 52, and pushes out the fastener 10A inserted into the piercing device 52 from the tip end of the piercing device 52.

In the applicator main unit 51, there are provided a piercing device operation portion 56 and a stylet operation portion (a fastener pusher operation portion) 57. Both the piercing device 52 and the stylet 53 have flexibility, and are arranged coaxially. They constitute an insertion portion 60 that is inserted through a work channel of an endoscope. Obviously, the insertion portion 60 is longer than the work channel of the endoscope.

A tip end surface of the piercing device 52 is formed diagonally with respect to the longitudinal direction of the piercing device 52. As a result, a tip end of the piercing device 52 is finished sharp. A base end of the piercing device 52 is connected with the piercing device operation portion 56, which is provided to a rear portion of the applicator main unit 51.

A tip end of the stylet 53 is formed into a shape not sharp but smooth. A base end of the stylet 53 is connected with the stylet operation portion 57, which is provided in the interior of the piercing device operation portion 56.

The piercing device operation portion 56 includes a cylindrical first shaft 56a that is inserted into the inside of the applicator main unit 51 from a rear end thereof. The first shaft 56a has an outer diameter slightly smaller than the inner diameter of the rear portion of the applicator main unit 51. Therefore, the first shaft 56a is slidable with respect to an inner surface of the rear portion of the applicator main unit 51. The base end of the piercing device 52 is fixedly attached to a tip end surface of the first shaft 56a, which is inserted into the applicator main unit 51, so that the longitudinal direction of the piercing device 52 coincides with that of the first shaft 56a. The piercing device 52 is capable of changing the relative position between itself and the applicator main unit 51 by sliding the first shaft 56a with respect to the applicator main unit 51.

In the rear portion of the applicator main unit 51, there is formed a female thread hole in a radial direction of the applicator main unit 51. Into this female thread, there is screwed a male thread 61. A tip end of the male thread 61 protrudes inside the applicator main unit 51. On the other hand, in an outside surface of the first shaft 56a, there is formed a groove 56b along the longitudinal direction of the first shaft 56a. Into the groove 56b of the first shaft 56a inserted into the applicator main unit 51, there is loosely fit the tip end of the male thread 61. As a result, the groove 56b defines the range of movement of the first shaft 56a with respect to the applicator main unit 51. When the male thread 61 is further screwed into the female thread hole to press the tip end thereof against a bottom surface of the groove 56b, it is possible to hold the first shaft 56a at arbitrary position with respect to the applicator main unit 51.

The stylet operation portion 57 includes: a cylindrical second shaft 62 that is inserted into an inside of the first shaft 56a from a rear end thereof; a lever 63 that is swingably supported by the first shaft 56a that supports the piercing device 52; a torsion coil spring 64 for biasing the lever 63 in a direction for spacing the lever 63 away from the applicator main unit 51; and a link mechanism 65 for transforming a swing of the lever 63 into a linear movement along the piercing device 52 of the stylet 53.

The base end of the stylet 53 is inserted into an interior of the second shaft 62 from the tip end thereof It is fixedly attached to the second shaft 62 so that the longitudinal direction of the stylet 53 coincides with that of the second shaft 62. The stylet 53 is capable of changing the relative position between itself and the piercing device 52 by sliding the second shaft 62 with respect to the first shaft 56a.

The link mechanism 65 includes: a base material 66; a bracket 68; a bar 70; a plate member 72; and a compression coil spring 74. The base material 66 is fixed onto an outside surface of the first shaft 56a. The bracket 68 is pivotally supported by the base material 66. The lever 63 has a lower end fixed in the bracket 68. The bar 70 has one end pivotally supported by the bracket 68 and the other end pivotally supported by the base material 66. A pin 71 provided in the other end of the bar 70 is fit into an oval hole 76 with allowance, the oval hole 76 being formed in the base material 66 along a sliding direction of the second shaft 62.

In the plate member 72, there is formed a hole 73 with a diameter larger than the outer diameter of the second shaft 62. The second shaft 62 inserted into the first shaft 56a penetrates through this hole 73. The difference between the outer diameter of the second shaft 62 and the inner diameter of the hole 73 is very slight. When the plate member 72 is moved in the longitudinal direction of the second shaft 62, that is, in the insertion direction of the second shaft 62 into the first shaft 56a, as if the plate member 72 is inclined, the inner surface of the hole 73 interferes with an outer surface of the second shaft 62, producing friction. Thereby, the force applied to the plate member 72 acts on the second shaft 62.

The compression coil spring 74 is disposed in an interior of the first shaft 56a. It biases the plate member 72 in a direction opposite to the insertion direction of the second shaft 62 into the first shaft 56a.

When the lever 63 is moved in a direction of going closer to the applicator main unit 51, the bar 70 is pulled to the front direction of the applicator main unit 51 via the bracket 68, causing the other end of the bar 70 to move along the oval hole 76. The plate member 72 is pressed by the other end of the bar 70 to move in the insertion direction of the second shaft 62 into the first shaft 56a while resisting the compression coil spring 74. At this time, the plate member 72 is slightly inclined to produce friction between itself and the second shaft 62. As a result, the force applied to the plate member 72 acts on the second shaft 62, causing the second shaft 62 to be pushed into the first shaft 56a. When the lever 63 is released, the torsion coil spring 64 spaces the lever 63 away from the applicator main unit 51. In addition, the compression coil spring 74 pushes the plate member 72 back to an initial position without producing friction between the plate member 72 and the second shaft 62.

The length of movement of the other end of the bar 70 for one operation on the lever 63 is always constant. Accordingly, an insertion length of the second shaft 62 into the first shaft 56a for one operation on the lever 63 is always constant as well. Therefore, it is possible to control the insertion length of the second shaft 62 into the first shaft 56a, that is, the insertion length of the stylet 53 into the piercing device 52 according to the number of operations on the lever 63. This means that it is possible to control the length of the fastener 10A which is pushed out from the tip end of the piercing device 52 according to the number of operations on the lever 63.

Here, when the fastener 10A is of a coil shape, it is preferable that the insertion length of the stylet 53 for one operation on the lever 63 be substantially n times or substantially 1/n (n is a natural number) the circumference of the fastener 10A. For example, if the insertion length of the stylet 53 for one operation on the lever 63 is substantially equal to the circumference of the fastener 10A, one revolution of the fastener 10A is pushed out from the tip end of the piercing device 52 for each operation on the lever 63. If the length of the second fixation portion 12 is equal to two revolutions of the fastener 10A, it is possible to push out only the second fixation portion 12 from the tip end of the piercing device 52 through two operations on the lever 63. If the insertion length of the stylet 53 for one operation on the lever 63 is substantially equal to a half circumference of the fastener 10A, a half revolution of the fastener 10A is pushed out from the tip end of the piercing device 52 for each operation on the lever 63. Furthermore, if the length of the second fixation portion 12 is equal to two revolutions of the fastener 10A, it is possible to push out only the second fixation portion 12 from the tip end of the piercing device 52 through four operations on the lever 63.

Into a tip end of the applicator main unit 51, there is inserted a pipe sleeve 80. On the pipe sleeve 80, there is formed an inside screw. By screwing this inside screw into a pipe sleeve 8 of an endoscope 2, it is possible to fix the applicator 50 to the endoscope 2. In an outside surface of the pipe sleeve 80, there is formed a groove 81 along a circumferential direction. On the other hand, on the applicator main unit 51, there is formed a female thread hole in a radial direction of the applicator main unit 51. Into this female thread hole, there is screwed a male thread 82. A tip end of the male thread 82 protrudes inside the applicator main unit 51. Into the groove 81 of the pipe sleeve 80, the tip end of the male thread 82 is loosely fit. As a result, it is possible to freely rotate the applicator main unit 51 with respect to the pipe sleeve 80 fixed on the endoscope 2. When the male thread 82 is further screwed into the female thread hole to press the tip end thereof against a bottom surface of the groove 81, it is possible to hold the applicator main unit 51 at arbitrary position with respect to the pipe sleeve 80.

Figure 4:
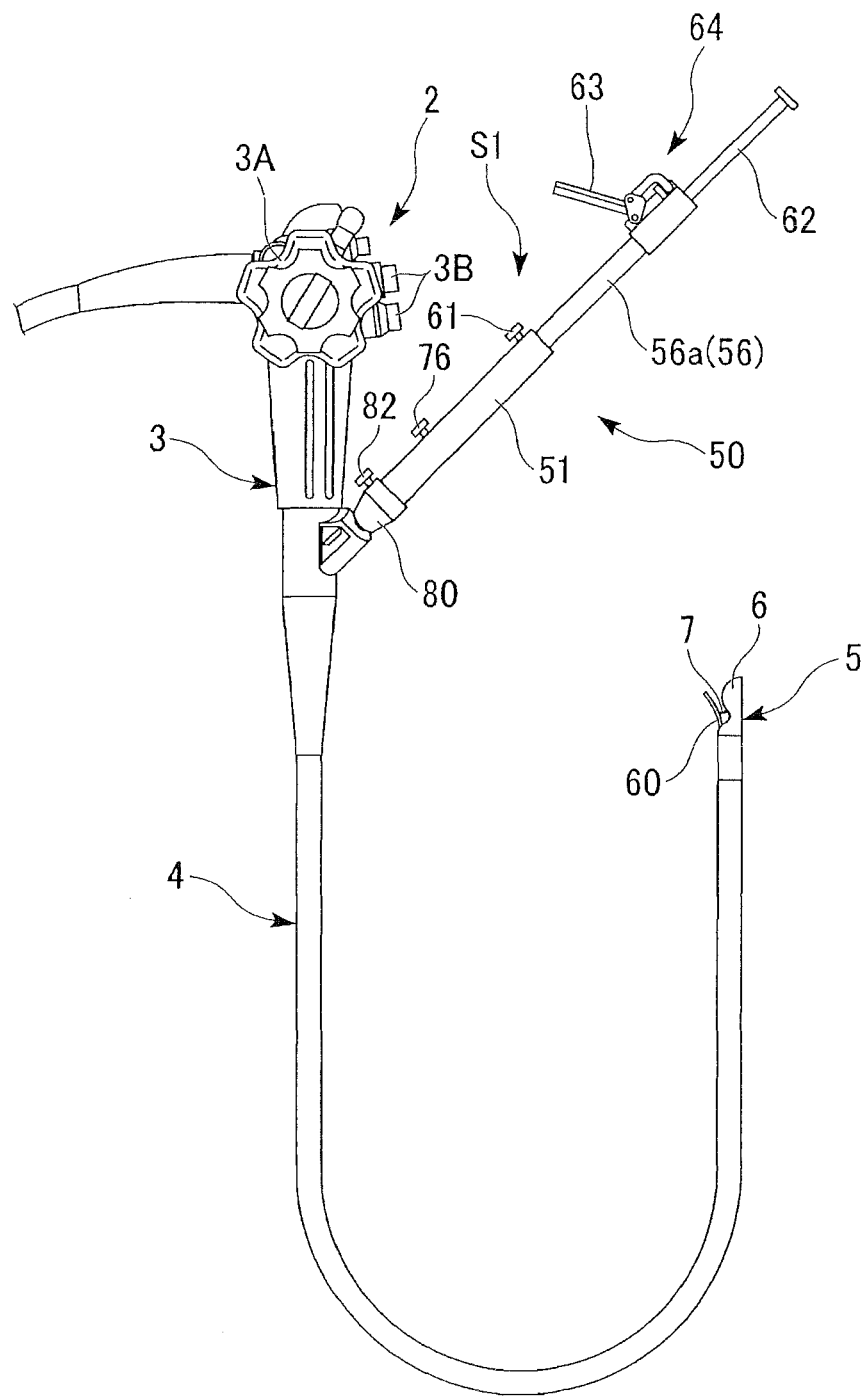
FIG. 4 shows a state in which the tissue fastening apparatus is inserted into a work channel of an endoscope and an applicator is fixed to the endoscope.

FIG. 4 shows a linear scanning ultrasonic endoscope as an endoscope 2 for use with the tissue fastening apparatus S1. This endoscope 2 includes a flexible insertion portion 4 extending from an operation portion 3 for use outside the body. To the operation portion 3, there are disposed: a knob 3A for curving a tip end portion of the insertion portion 4; and various buttons 3B. To a tip end of the insertion portion 4, there is attached a cover 5. To this cover 5, there is attached an ultrasonic apparatus 6. The ultrasonic apparatus 6 swells out on a plane including an axis line of the insertion portion 4. It has a plurality of ultrasonic transducers arranged along an arc-shaped outer circumference. Furthermore, the endoscope 2 is provided with an elevator 7 so that the tip end of the applicator 50 can be sent out laterally. With an operation on the elevator 7 at proximal side, it is possible to adjust the orientation (angle) of an insertion portion 60 of the applicator 50 which is sent out from the tip end of the insertion portion 4. Note that the endoscope 2 may be provided with an ultrasonic apparatus of other probe type. In addition, an endoscope without an ultrasonic apparatus 6 may be used. In this case, an ultrasonic apparatus for use outside the body, or an X-ray apparatus, a magnetic resonance imaging (MRI) system, or a CT (Computerizing Tomography) apparatus are additionally used appropriately.

Figure 5:
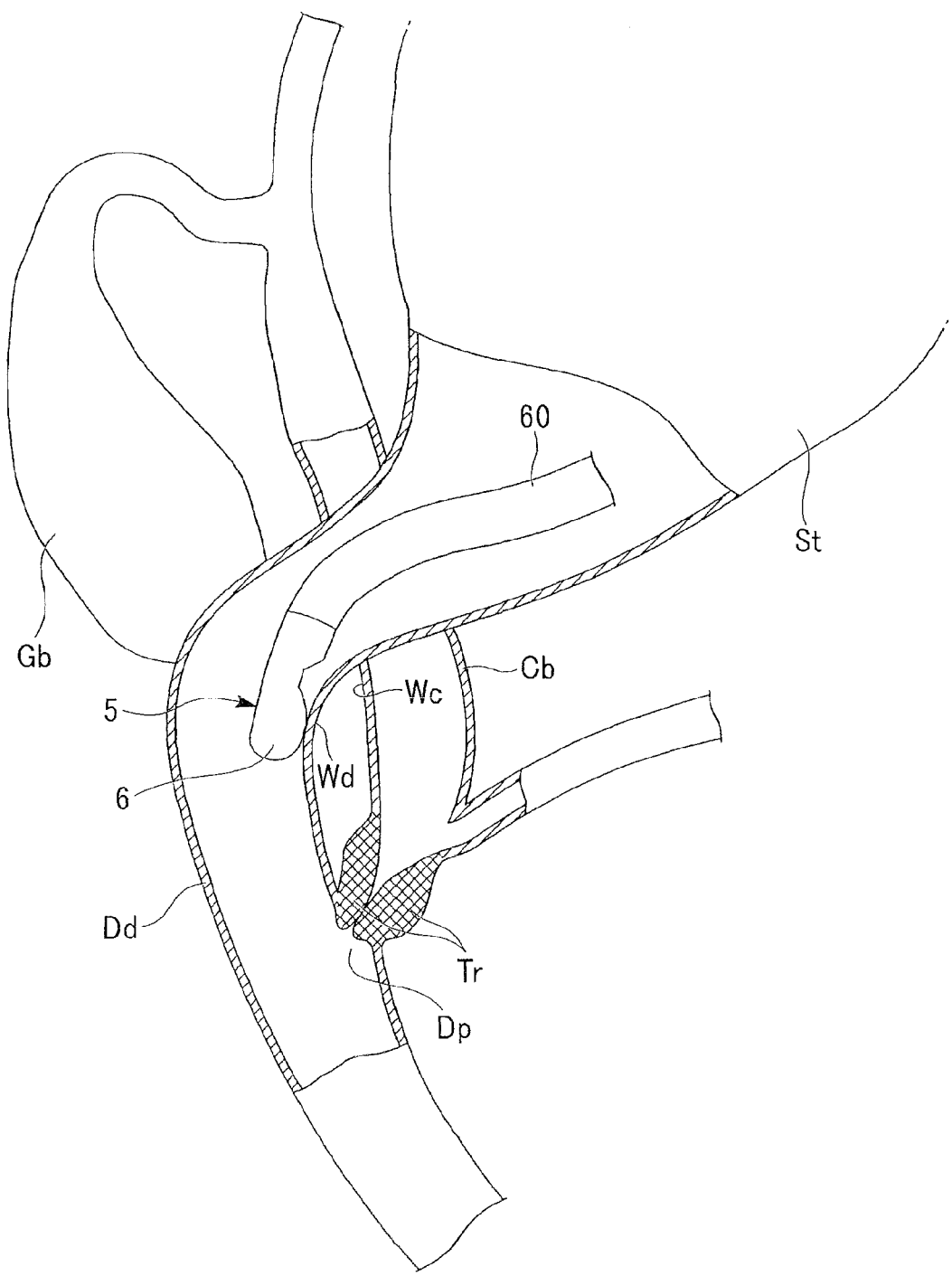
FIG. 5 shows a state in which an insertion portion of the endoscope is inserted into a duodenum.

Next is a description of an operation of the tissue fastening apparatus S1 configured as above, taking as an example the manipulation of closely fixing a duodenum (first tissue) onto a common bile duct (second tissue) to communicate both. Such a manipulation is executed for example in the case where bile is mixed into blood to develop jaundice as a result of an inability to discharge bile due to obstruction of a duodenal papilla Dp by a tumor Tr, as shown in FIG. 5. With this manipulation, it is possible to discharge bile directly from a common bile duct Cb to a duodenum Dd.

First, the insertion portion 4 of the endoscope 2 is inserted from the mouth of a patient. The endoscope 2 is inserted into the duodenum Dd, which is an upper gastrointestinal tract. With the ultrasonic apparatus 6, the state of the outside of the duodenum Dd is checked for a site appropriate for the manipulation, the site being on a side closer to a stomach St side than a duodenal papilla Dp and being close to the common bile duct Cb.

Figure 6:
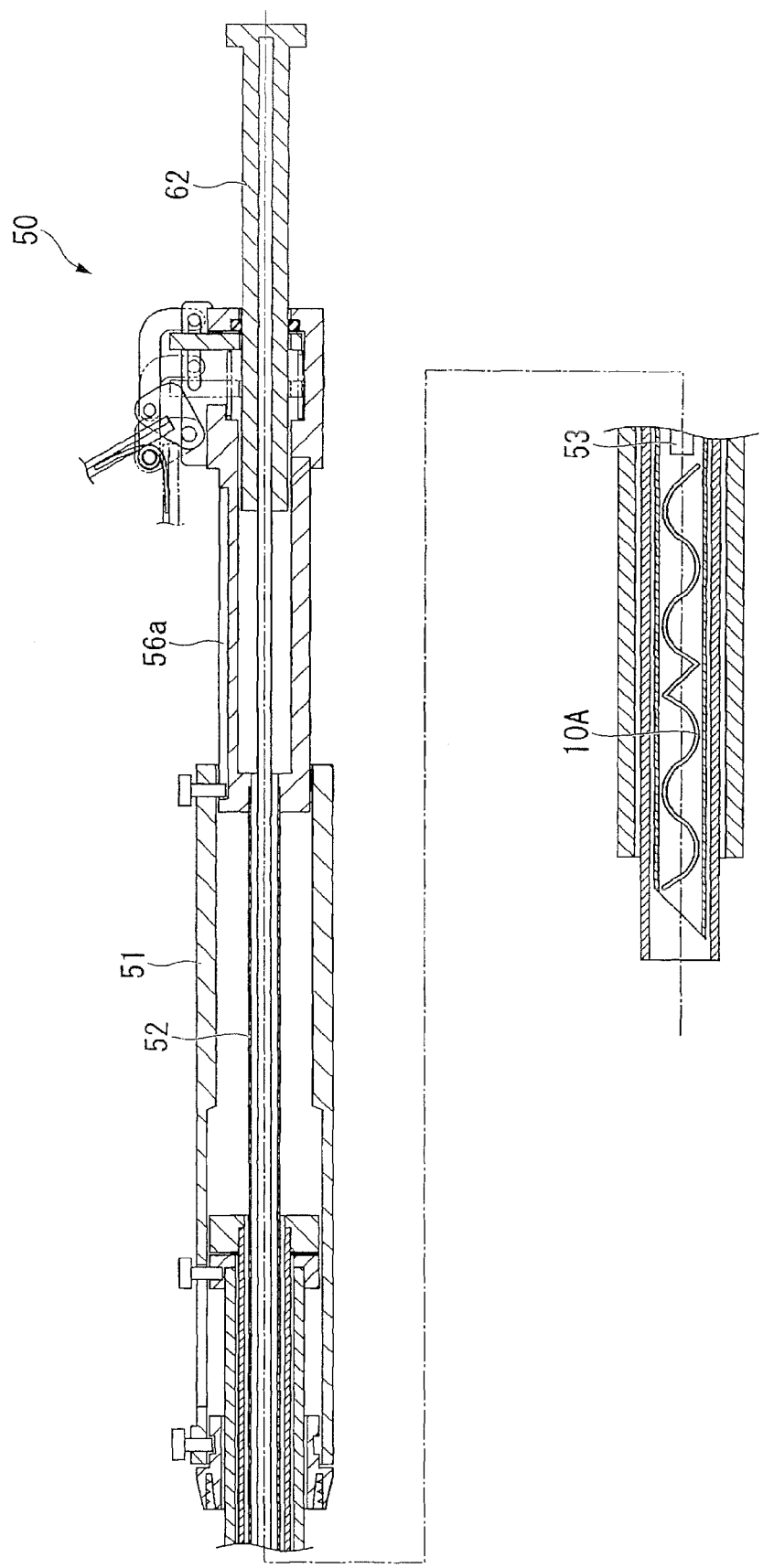
FIG. 6 to FIG. 10 are cross-sectional views showing how an applicator is used in the respective steps of performing manipulation for fixing a common bile duct onto a duodenum and communicating both organs.

In the applicator 50, as shown in FIG. 6, the first shaft 56a is previously operated to move back the piercing device 52 with respect to the applicator main unit 51. In addition, the second shaft 62 is previously operated to move back the stylet 53 with respect to the applicator main unit 51.

The insertion portion 60 of the applicator 50 is inserted into a work channel of the endoscope 2 and then is moved forward, to thereby fix the applicator 50 onto the endoscope 2. As a result, the tip end of the insertion portion 60 is caused to protrude from the tip end of the insertion portion 4 of the endoscope 2. Then, the orientation of the protruded insertion portion 60 is adjusted with the elevator 7.

Figure 7:
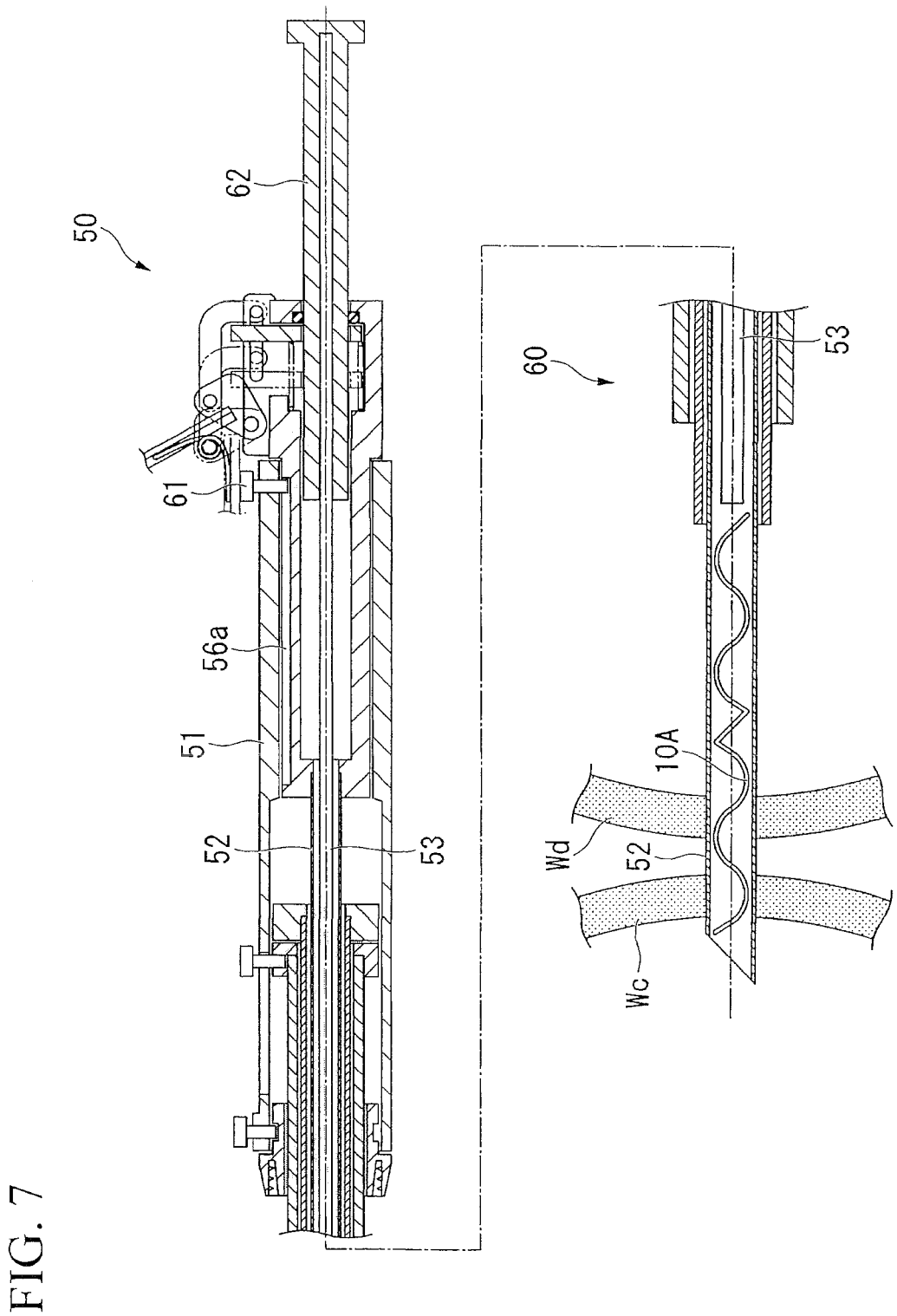

The ultrasonic apparatus 6 provided to the endoscope 2 is used to scan the common bile duct Cb across the duodenum Dd to determine the position at which the piercing device 52 is piercingly inserted into the common bile duct Cb. Then, as shown in FIG. 7, the male thread 61 is loosened and the first shaft 56a is pushed into the applicator main unit 51 to protrude the tip end of the piercing device 52. As a result, the sharp tip end of the piercing device 52 is piercingly inserted through an intestinal wall Wd of the duodenum Dd from the inside to the outside, and subsequently is piercingly inserted through a duct wall Wc of the common bile duct Cb from the outside to the inside. Then, the male thread 61 is tightened to fix the first shaft 56a onto the applicator main unit 51.

Figure 8:
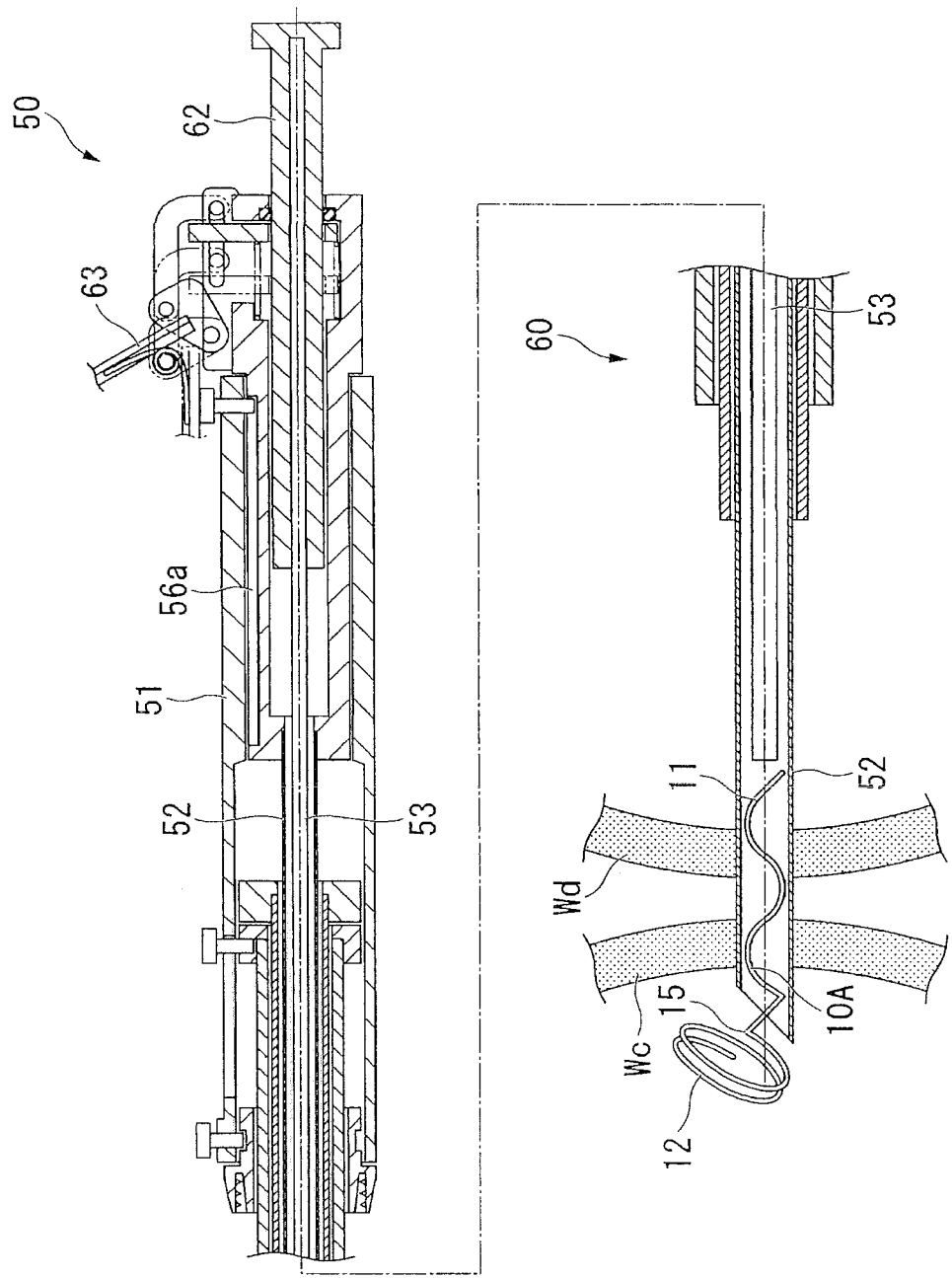

As shown in FIG. 8, the lever 63 is operated to push the second shaft 62 into the first shaft 56a by a predetermined length. For example, the lever 63 is operated a predetermined number of times. As a result, the stylet 53 changes its relative position to the piercing device 52. Thereby, the second fixation portion 12 of the fastener 10A is pushed out from the tip end of the piercing device 52. The second fixation portion 12, when pushed out from the piercing device 52, assumes its original coil shape, and is locked on the inside of the duct wall Wc of the common bile duct Cb.

The male thread 61 is loosened. The first shaft 56a is pulled out a little from the applicator main unit 51 to shorten the protrusion length of the piercing device 52. Then, the male thread 61 is tightened to fix the first shaft 56a onto the applicator main unit 51. As a result, the tip end of the piercing device 52 is spaced apart a little from the inside surface of the intestinal wall Wd of the duodenum Dd.

Figure 9:
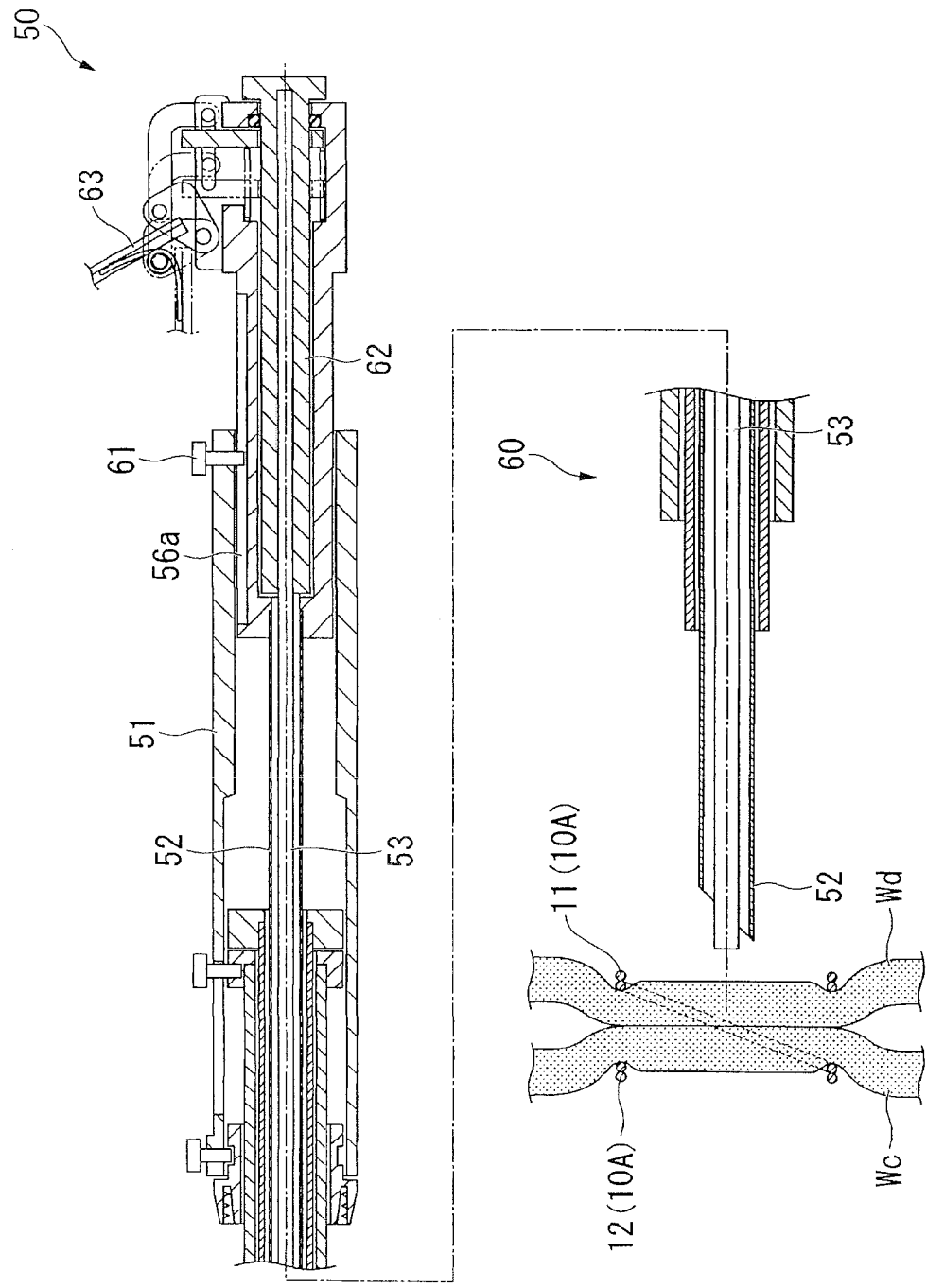

As shown in FIG. 9, the lever 63 is operated again to push the second shaft 62 into the first shaft 56a by a predetermined length. For example, the lever 63 is operated a predetermined number of times. As a result, the stylet 53 changes its relative position to the piercing device 52. Thereby, the linking portion 13 and the first fixation portion 11 of the fastener 10A are pushed out from the tip end of the piercing device 52. The first fixation portion 11, when pushed out from the piercing device 52, assumes its original coil shape, and is locked on the inside of the intestinal wall Wd of the duodenum Dd.

The fastener 10A, when pushed out from the piercing device 52, clamps the duodenum Dd and the common bile duct Cb so as to cause the intestinal wall Wd of the duodenum Dd locked by the first fixation portion 11 and the duct wall Wc of the common bile duct Cb locked by the second fixation portion 12 to press against each other.

Figure 10:
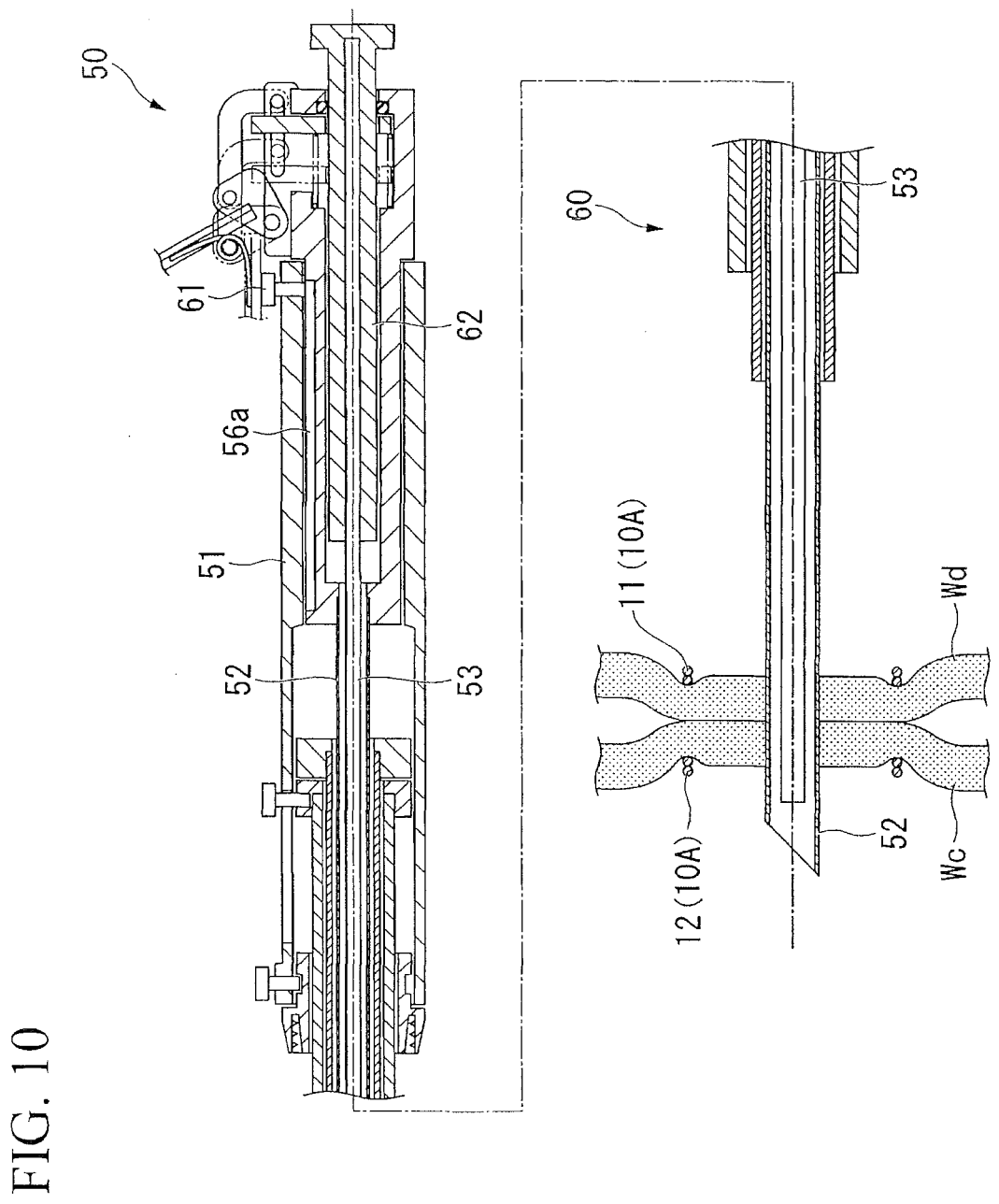
Figure 11:
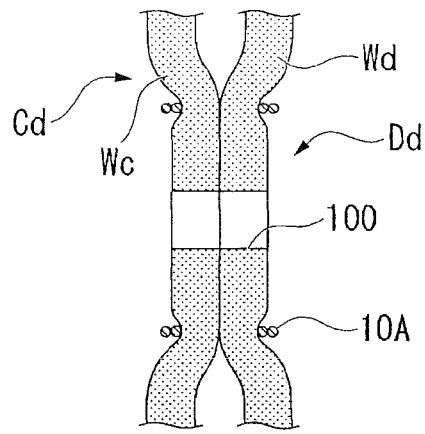
FIG. 11 to FIG. 13 show a formation process of a fistula.

As shown in FIG. 10, the second shaft 62 is pulled a little to retract the tip end of the stylet 53 inside the piercing device 52. Then, the male thread 61 is loosened. The first shaft 56a is again pushed into the applicator main unit 51 to protrude the tip end of the piercing device 52. As a result, the sharp tip end of the piercing device 52 is piercingly inserted through the intestinal wall Wd of the duodenum Dd and the duct wall Wc of the common bile duct Cb inside the fastener 10A, to thereby form a through-hole 100 in the tissue bound by the fastener 10A, as shown in FIG. 11. If the smooth tip end of the stylet 53 is protruded from the sharp tip end of the piercing device 52 after formation of the though-hole 100, the possibility of the sharp tip end of the piercing device 52 carelessly injuring the surrounding tissue is eliminated.

When the fastener 10A is left in a living body, the intestinal wall Wd of the duodenum Dd and the duct wall Wc of the common bile duct Cb are compressed by the fastener 10A, putting the body tissue inside the loop of the fastener 10A in an ischemic state. A continued ischemic state necrotizes the body tissues. On the other hand, outside the loop of the fastener 10A, fibril formation is occurred in the intestinal wall Wd and the duct wall Wc and the intestinal wall Wd and the duct wall Wc are adhered over the entire circumference of the fastener 10A.

Figure 12:
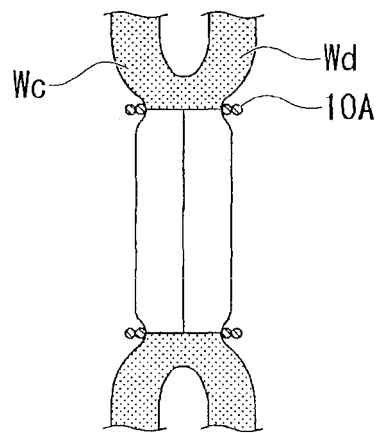

As a result, the necrotized body tissues falls off from the intestinal wall Wd and the duct wall Wc, as shown in FIG. 12. After that, the fastener 10A supported by that body tissues falls off from the intestinal wall Wd and the duct wall WC accordingly. The fastener 10A is excreted out of the body.

Figure 13:
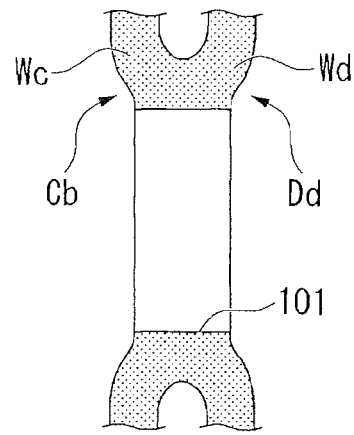

Finally, in the intestinal wall Wd and the duct wall Wc from which the necrotized body tissues and the fastener 10A have fallen off, there is formed a fistula 101 that communicates the duodenum with the common bile duct, as shown in FIG. 13. Through this fistula 101, bile is discharged from the common bile duct Cb to the duodenum Dd. As described above, the margin of the fistula 101 is adhered over the entire circumference. Therefore, bile will not leak into the abdominal cavity from between the intestinal wall Wd and the duct wall Wc.

By using the applicator 50, an operation on the lever 63, as if to grasp it lightly, allows the tissue fastener 10A to be pushed out from the piercing device 52 easily and accurately. As a result, it is possible to suitably leave the fastener 10A at a desired position in a living body.

Next is a description of a behavior of the fastener 10A that is pushed out from the tip end of the piercing device 52.

The fastener 10A is first pushed out so as to protrude only the second fixation portion 12 from the tip end of the piercing device 52 that has been piercingly inserted through the intestinal wall Wd of the duodenum Dd and the duct wall Wc of the common bile duct Cb. The second fixation portion 12, in the process of being pushed out from the tip end of the piercing device 52, successively assumes its original coil shape, and is locked on the duct wall Wc of the common bile duct Cb.

The second fixation portion 12, in the process of being pushed out from the tip end of the piercing device 52, generates force for restoring its own shape to its original coil shape. With this force acting on the duct wall Wc of the common bile duct Cb, the fastener 10A tends to be pulled inside the common bile duct Cb by an amount more than the push-out amount of the stylet 53. However, the fastener 10A is provided with the linking portion 13 between the first fixation portion 11 and the second fixation portion 12. In addition, the bent portion 15 is formed between the second fixation portion 12 and the linking portion 13. As a result, if the whole of the second fixation portion 12 is pushed out, the second tissue fixation portion 12 changes orbit from one in the process of being pushed out from the tip end of the piercing device 52. This is because when the bent portion 15 of the fastener 10A is pushed out from the tip end of the piercing device 52, the second fixation portion 12 that is released from the restraint by the piercing device 52 changes its orientation depending on the angle of the bent portion 15. With the changed in orientation of the second fixation portion 12, even if force is generated in the second fixation portion 12 for restoring its own shape to its original coil shape, the force ceases to act on the duct wall Wc of the common bile duct Cb. Therefore, the fastener 10A will not be pulled inside the common bile duct Cb by more than a push-out amount of the stylet 53.

After that, the whole fastener 10A including the remaining first fixation portion 11 is pushed out from the tip end of the piercing device 52, which has been pulled out from the intestinal wall Wd of the duodenum Dd and the duct wall Wc of the common bile duct Cb. The first fixation portion 11, in the process of being pushed out from the tip end of the piercing device 52, successively assumes its original coil shape, and is locked on the intestinal wall Wd of the duodenum Dd.

With the first fixation portion 11 locked on the intestinal wall Wd of the duodenum Dd and the second fixation portion 12 locked on the duct wall Wc of the common bile duct Cb, the intestinal wall Wd and the duct wall Wc are clamped. The linking portion 13 is left in the interiors of the intestinal wall Wd and the duct wall Wc that are clamped. Because the gap G is provided between the first fixation portion 11 and the second fixation portion 12, the intestinal wall Wd and the duct wall Wc are clamped so that they press against each other with uniform force.

It is preferable that the angle θ1 of the linking portion 13 with respect to the first fixation portion 11 and the angle θ2 of the linking portion 13 with respect to the second fixation portion 12 both be 45° or less (see FIG. 3). If the angles θ1, θ2 are larger than 45°, the bent portion 14 forming the angle θ1 and the bent portion 15 forming the angle θ2 come into contact with the internal surface of the piercing device 52 in the process of pushing out the fastener 10A from the tip end of the piercing device 52, thereby producing strong frictional force. This makes it difficult to smoothly push out the fastener 10A from the piercing device 52.

It is preferable that the gap G between the first fixation portion 11 and the second fixation portion 12 be 15 mm or less. If the gap C is 15 mm or less, it is possible to fix body tissue by use of the applicator 50, in substantially all the organs which can be approached using the endoscope 2.

However, a plural types of tissue fastener 10A with difference in the size of the gap G may be provided in order to offer an optional selection according to the thickness of the organ to be treated or to characteristics of individual patients. As a result, an appropriate selection of an optimal fastener makes it possible to perform a suitable treatment in various situations.

Figure 14:
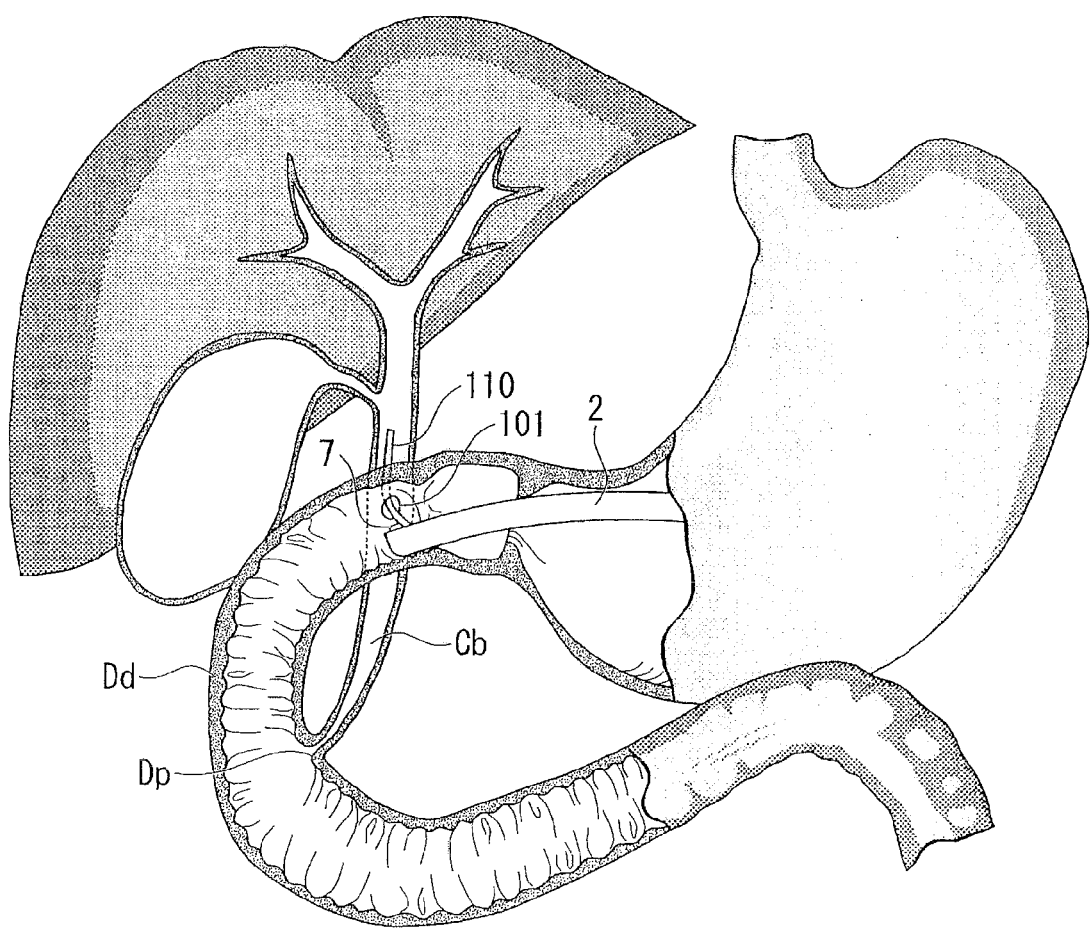
FIG. 14 shows one example of a treatment method of a first embodiment according to the present invention.
Figure 15:
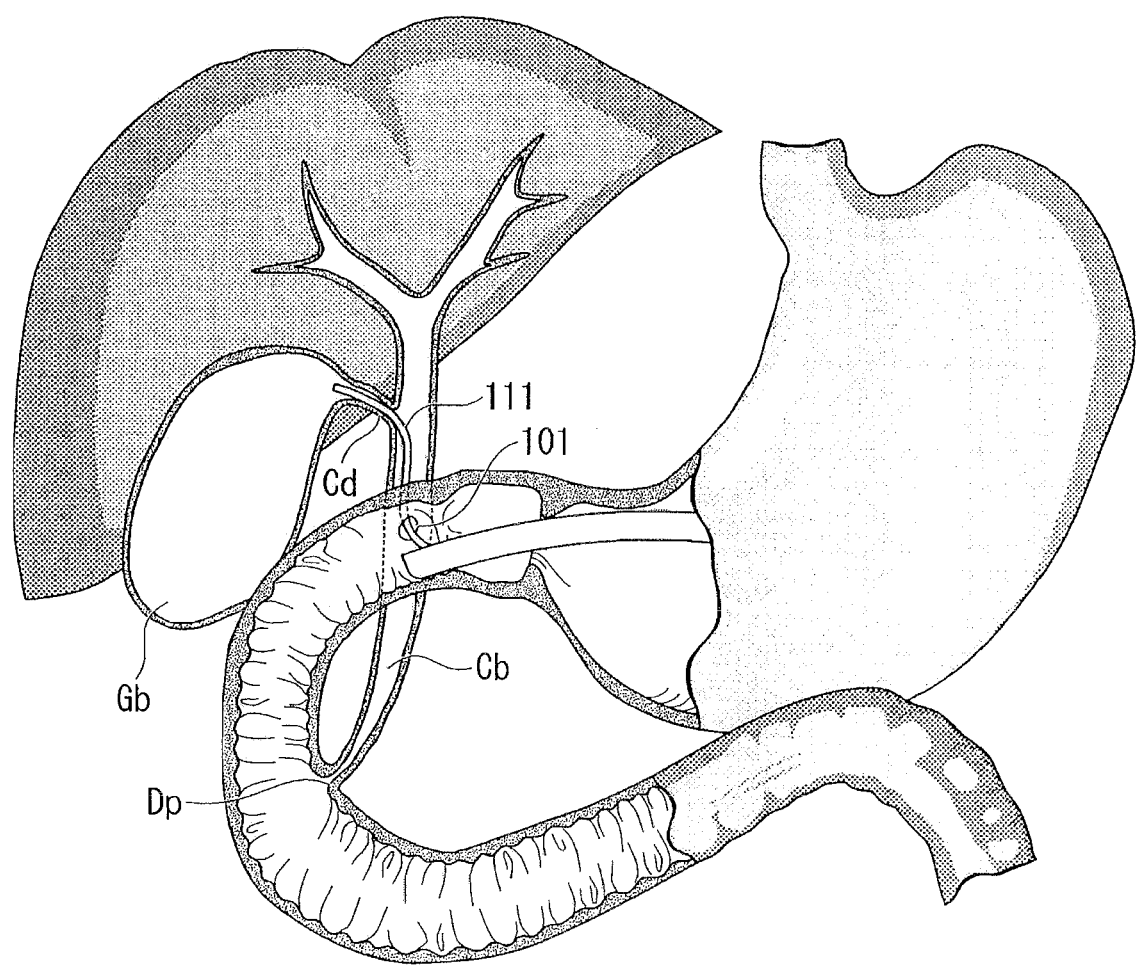
FIG. 15 shows another example of a treatment method of the same embodiment.

Next is a description of the first embodiment of a treatment method according to the present invention using the tissue fastening apparatus S1 configured as above, with reference to FIG. 14 and FIG. 15.

FIG. 14 shows a state in which the tissue fastening apparatus S1 is used to perform an endoscopic retrograde cholangiography (ERC) on a bile duct.

First, the user uses a tissue fastening apparatus S1 to form a fistula 101 at a site where a duodenum Dd is adjacent to a common bile duct Cb, in the aforementioned procedure. Next, the user moves the tip end of an endoscope 2 to the vicinity of the fistula 101, and protrudes a catheter 110 for injecting a contrast medium while adjusting a protrusion angle with an elevator 7. Then, the user inserts a tip end of the catheter 110 into the bile duct from the fistula 101, and moves it to an upstream side. After bringing the tip end to a desired position, the user injects a contrast medium from the tip end of the catheter 110 to make the bile duct contrastively visible.

In the conventional ERC, in the case such as of making a bile duct on the upstream side of the common bile duct visible, it is necessary to reversely move the catheter for a comparatively long distance. Furthermore, the duodenal papilla Dp looks downward. Therefore, the angle at which the catheter is protruded from the endoscope becomes acute, which makes it difficult to operate the elevator. Furthermore, the duodenal papilla Dp is normally closed by the sphincter. Therefore, to insert the catheter into the bile duct, it is necessary for the catheter to go through the sphincter.

These factors make the conventional ERC a manipulation requiring a manipulator to have skills to a certain degree. However, in the aforementioned ERC as the treatment method according to the present embodiment, the fistula 101 is formed, which allows the catheter to move forward to the further upstream side of the bile duct with ease without going through the sphincter. Therefore, it is possible to perform manipulation of cholangiography more easily and more safely.

Furthermore, it is often found that the adjacent area between the duodenum Dd and the common bile duct Cb in which the fistula 101 is to be formed does not typically go downward but runs substantially horizontally. Accordingly, the angle at which the catheter 110 is protruded from the endoscope 2 becomes gentler compared with the case of the conventional ERC. Therefore, operation on the elevator 7 becomes also easier, allowing manipulation to be performed with ease.

The treatment method using a treatment device with a lumen as in the present embodiment is not limited to the aforementioned ERC. For example, as shown in FIG. 15, a tube 110A, which is a treatment device with a lumen, may be moved forward into a cystic duct Cd through substantially the same operation as that of the aforementioned ERC and various manipulations may be performed.

To be more specific, for example, cholecystography by supplying a contrast medium is feasible. Furthermore, in the case such as of obstruction of a cystic duct Cd, drainage may be performed by sucking the bile accumulated in a gallbladder Gb. Furthermore, the supply of a drug solution from the tube 110A makes it possible to dissolve a gallstone, or to necrotize mucosa of the gallbladder to thereby destroy the ability to from a gallstone. In the conventional manipulation, it is required for the treatment device, after entry from the duodenal papilla Dp and reverse movement through the common bile duct Cb, to further move into the cystic duct Cd. Therefore, such a manipulation is strikingly difficult. However, in the treatment method via the fistula 101 according to the present embodiment, it is possible to perform any of the above various manipulations with ease and without any special skills.

In the present embodiment, the example where the ERC is performed after formation of the fistula 101 has been described. Instead of this, the treatment device may be inserted into the bile duct via the through-hole 100. Even in the case of utilizing the through-hole 100, leakage of a contrast medium or the like into the abdominal cavity is prevented by the fastener 10A. Therefore, no problem is posed.

Figure 16A:
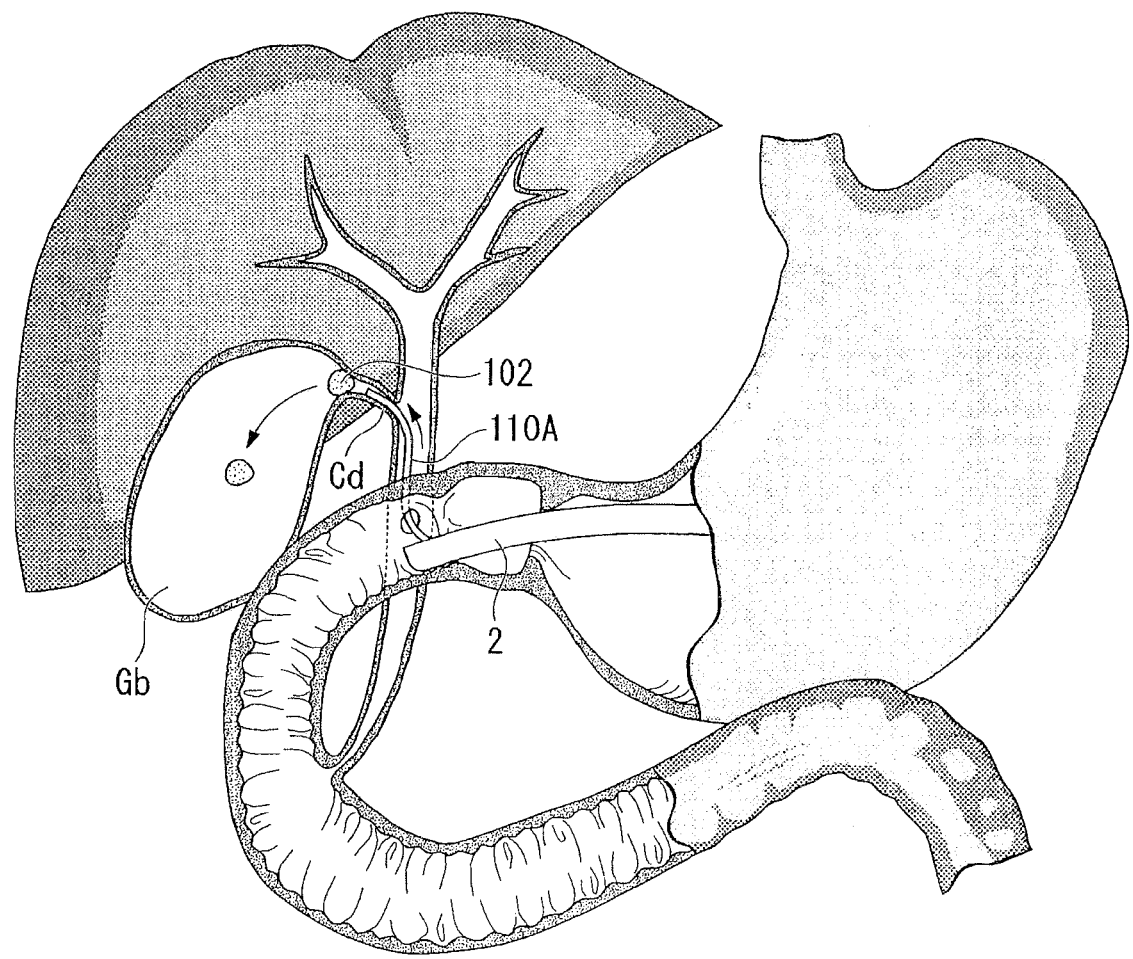
FIG. 16A to FIG. 16C show one example of a treatment method of a second embodiment according to the present invention.
Figure 16B:
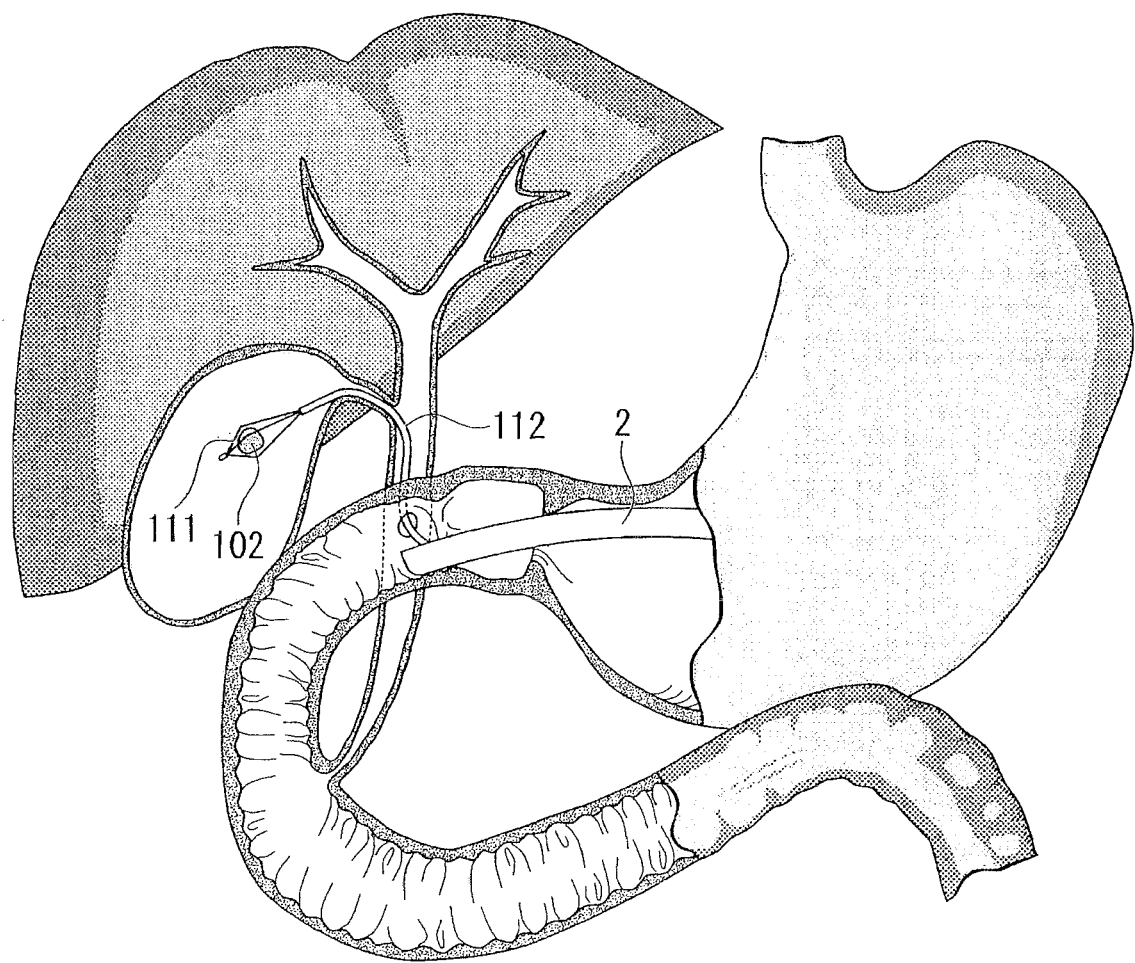
Figure 16C:
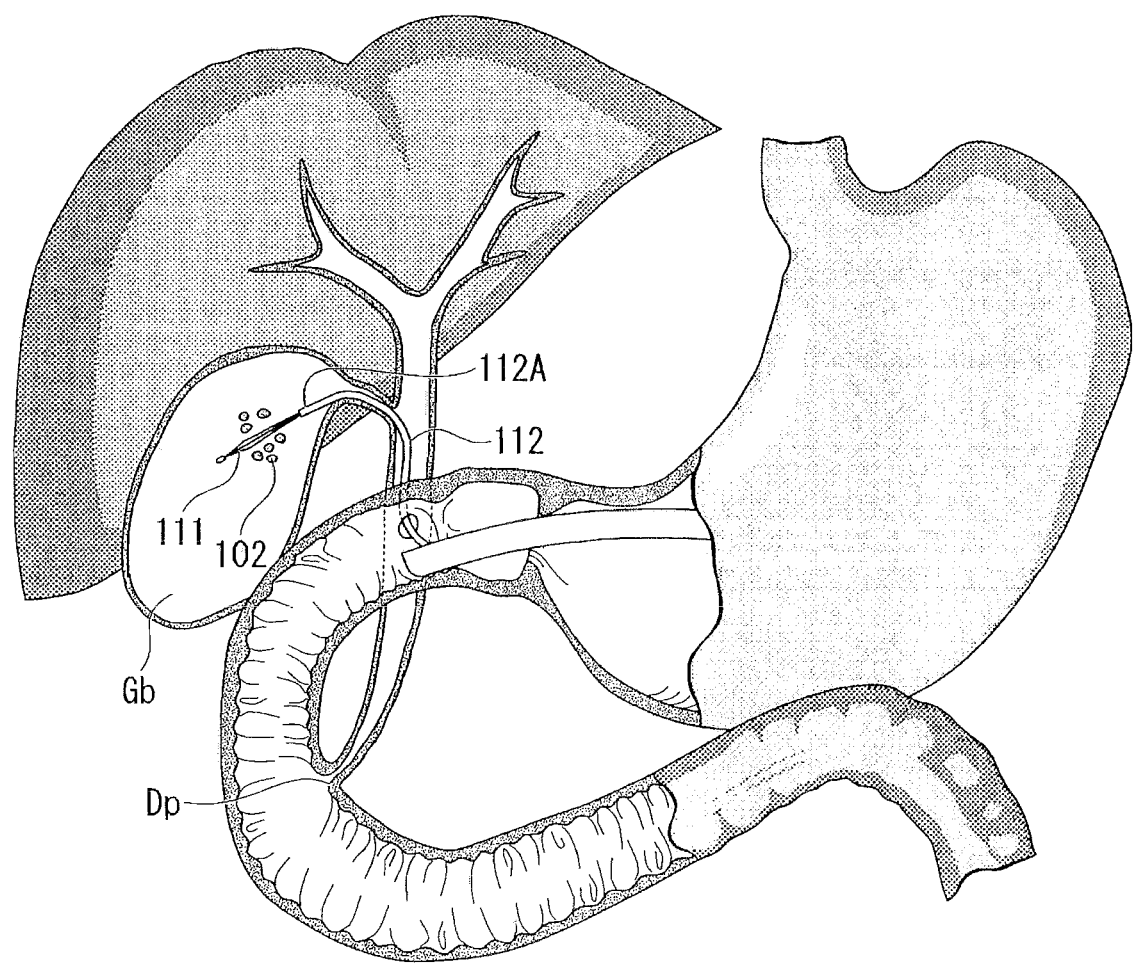

Next is a description of a treatment method of a second embodiment according to the present invention, with reference to FIG. 16A to FIG. 16C. In the description of the following embodiments, common constituent parts are designated with like reference numerals and are not repetitiously explained.

FIG. 16A is one example of a treatment method according to the present embodiment. It shows a procedure of removing an impacted calculus. As shown in FIG. 16A, when a calculus 102 formed in a gallbladder Gb is stuck in a joint portion with a cystic duct Cd and is turned to a state of an impacted calculus, an outflow of bile is prevented. Therefore, the patient complains of a subjective symptom such as a severe pain.

The user inserts a guide wire, a tube 110A with a larger diameter, or the like into an endoscope 2, and inserts the endoscope 2 into a cystic duct by the same method as in the first embodiment. The user then shoves the calculus 102 toward the gallbladder, with the inserted tube 110A or the like used as a pusher. As a result, when the calculus 102 falls in the gallbladder, the subjective symptom of the patient remarkably improves.

The user checks the size and the like of the calculus 102 by the X-ray fluoroscopy or the like. If there is a high probability of recurrence because the calculus 102 has a size larger than a predetermined size or for some other reason, the user performs a manipulation of crushing the calculus 102 as required.

FIG. 16B and FIG. 16C show a crushing operation of the calculus 102. The user pulls the treatment device, which has been used as a pusher, out of the endoscope 2 and then inserts a treatment device 112 with a known basket 111 provided at its tip end into a treatment device channel of the endoscope 2 and protrudes the treatment device 112. At this time, if using a guide wire as a pusher, the user may use the guide wire as a guide to insert the treatment device 112, instead of pulling out the guide wire.

The user takes the calculus 102 into a basket 111, and pulls the basket 111 into a sheath 112A of the treatment device 112, as shown in FIG. 16C, to thereby crushes the calculus 102. As a result, the calculus is broken into small pieces, and hence requires less effort to be discharged from the gallbladder Gb.

Also in the treatment method of the present embodiment, similarly to the aforementioned first embodiment, it is possible to perform manipulation after allowing the treatment device to easily reach the gallbladder, which rejects easy approach from the duodenal papilla Dp.

Furthermore, compared with the case where the gallbladder Gb and the duodenum Dd are communicated with each other, bile in an unconcentrated state is less likely to flow out into the duodenum. Therefore, it is possible to perform a medical treatment without reducing the ability of the patient to absorb fat.

Figure 17:
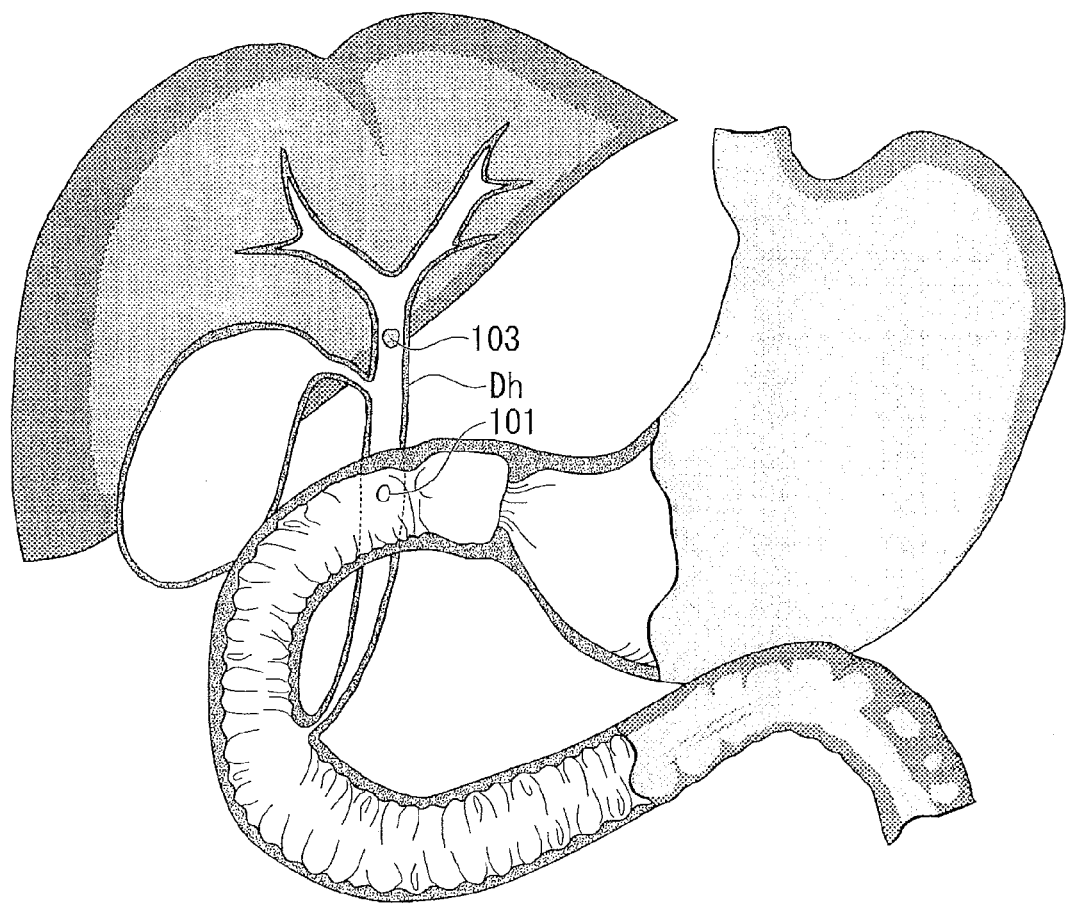
FIG. 17 and FIG. 18 show one example of a treatment method of a third embodiment according to the present invention.

Next is a description of a treatment method of a third embodiment according to the present invention. FIG. 17 to FIG. 20 show a procedure of removing a calculus in a common hepatic duct Dh, which is one example of the treatment method according to the present embodiment. As shown in FIG. 17, a calculus 103 has a diameter larger than that of a fistula 101 formed by a tissue fastening apparatus S1. Therefore, it is not possible to take the calculus 103 as it is out of the hepatic duct through the fistula 101.

Figure 18:
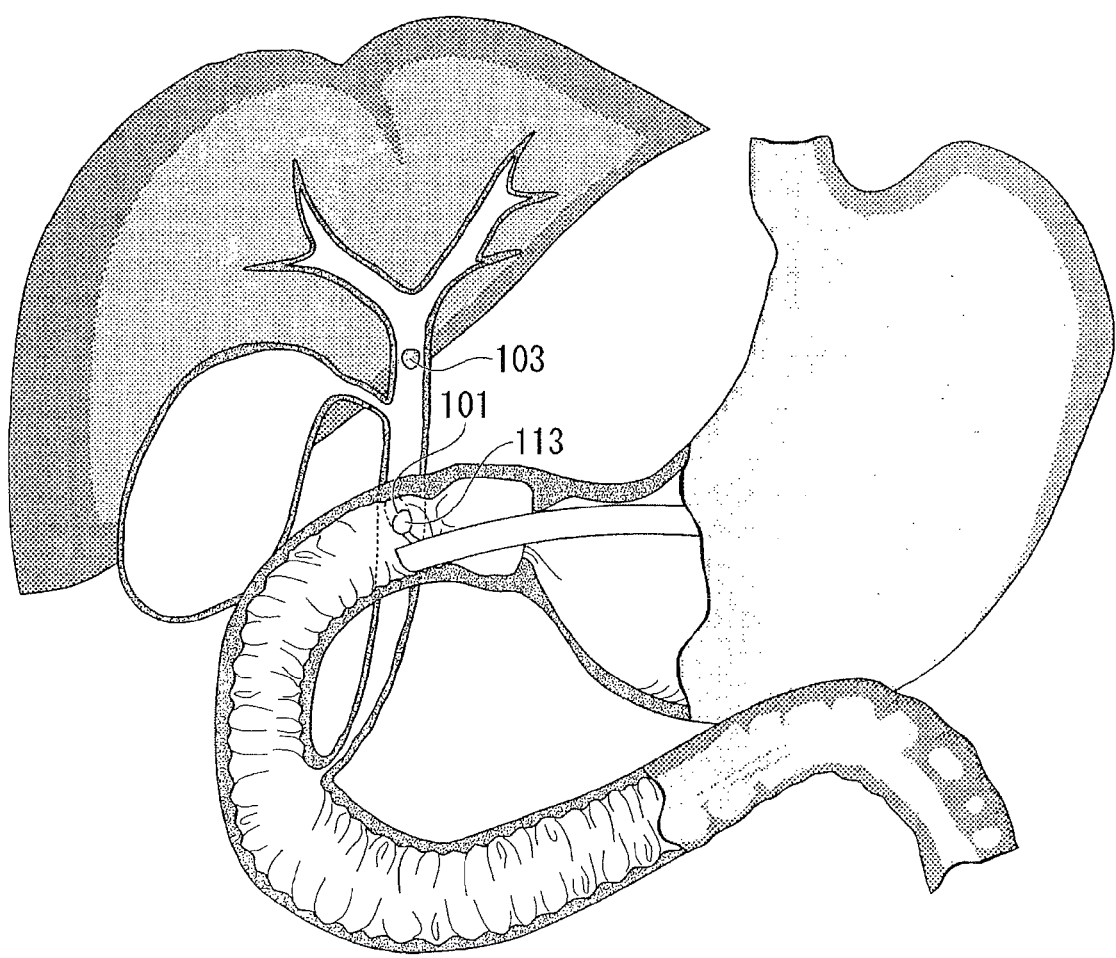
Figure 19:
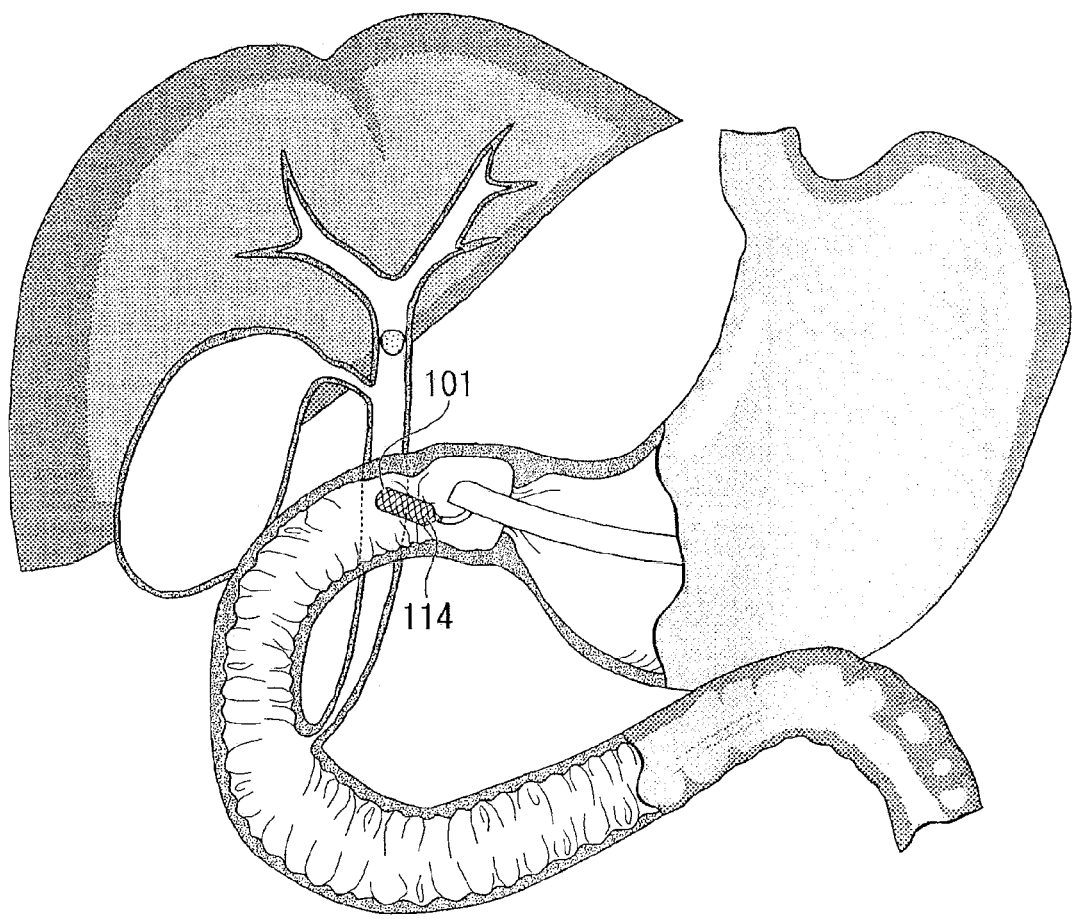
FIG. 19 shows another example of a treatment method of the same embodiment.

Therefore, as shown in FIG. 18, a known balloon 113 is inserted into the fistula 101, and the balloon 113 is expanded to make the diameter of the fistula 101 larger than that of the calculus 103. At this time, instead of using the balloon 113, a known metallic stent 114 with a self-expansion ability may be inserted into the fistula 101 to enlarge the diameter of the fistula 101, as shown in FIG. 19.

Figure 20:
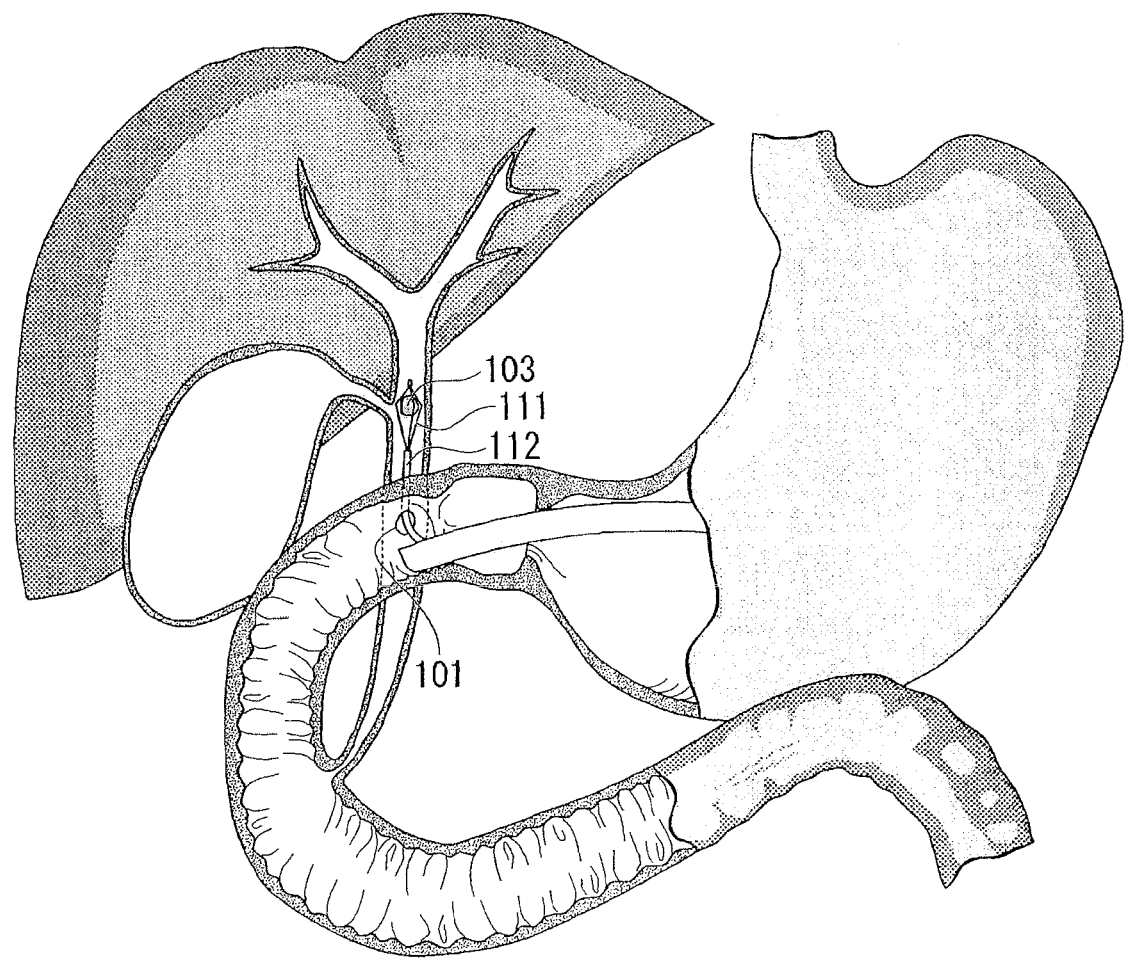
FIG. 20 shows a treatment method of the same embodiment.

After the enlargement of the diameter of the fistula 101, the user inserts a treatment device 112, takes the calculus 103 into a basket 111, and then removes the calculus 103 out of the bile duct through the fistula 101 as shown in FIG. 20. At this time, the calculus 103 may be appropriately crushed to adjust its size as required.

In the treatment method of the present embodiment, the diameter of the fistula 101 is enlarged to a desired size. Therefore, it is possible to smoothly remove foreign matter such as the calculus 103. Furthermore, the enlargement of the fistula makes it easy to discharge bile through the fistula. Therefore, it is possible to enhance the effect of curing jaundice.

Note that in expansion of the fistula 101, the tissue around the fistula is strongly extended. Therefore, it is preferable that this expansion manipulation be performed after the surrounding tissue is sufficiently adhered after formation of the fistula. In animal experiments, it is confirmed that in five to seven days after formation of a through-hole, the tissue surfaces in close contact are adhered after fibril formation and the like, and that the adhered area becomes stable in about two weeks. Therefore, safety is conceivably enhanced by the following procedure. A through-hole 100 is first formed with a tissue fastening apparatus S1, and then a series of the above manipulations is performed in five or more days, more preferably in two weeks or more days, after the formation.

Figure 21:
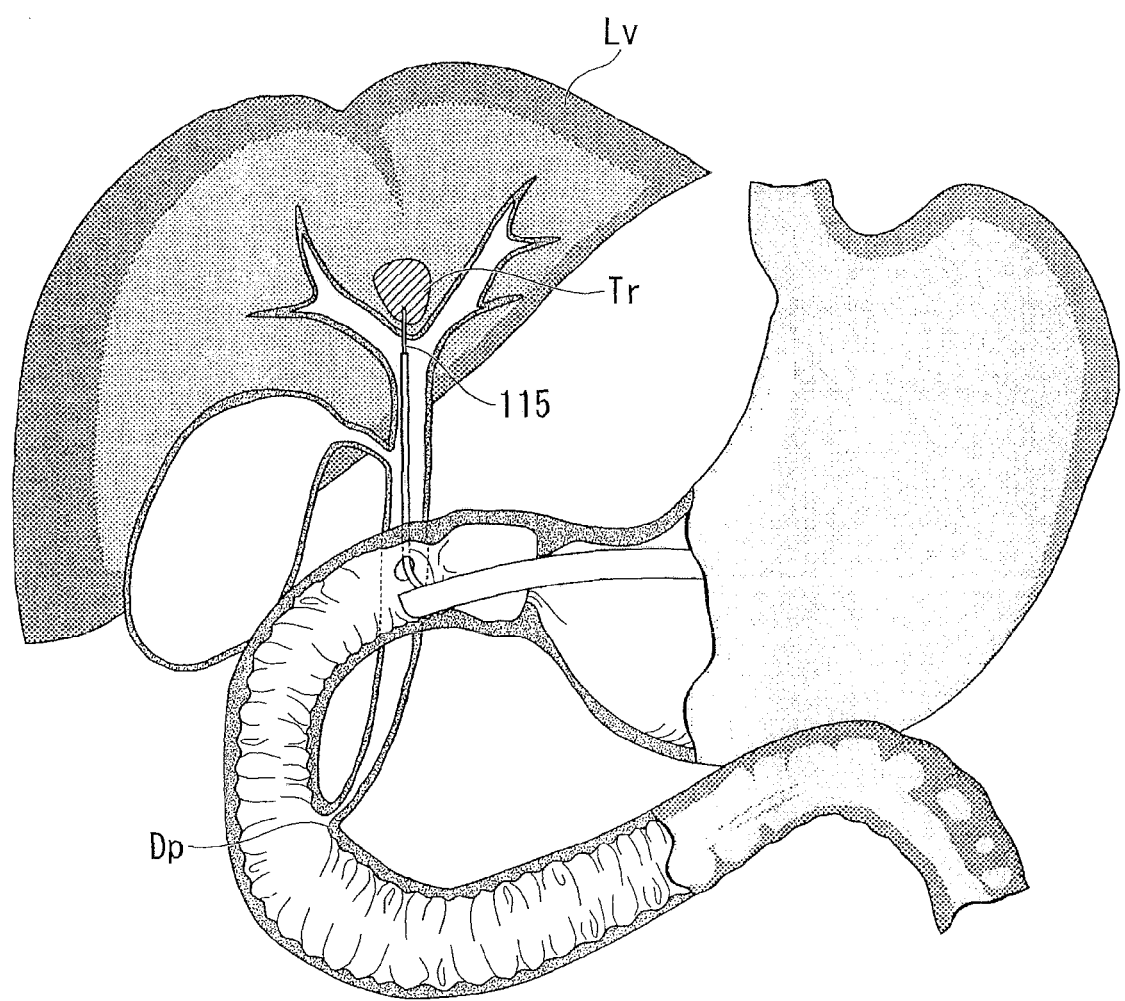
FIG. 21 shows one example of a treatment method of a fourth embodiment according to the present invention.
Figure 22:
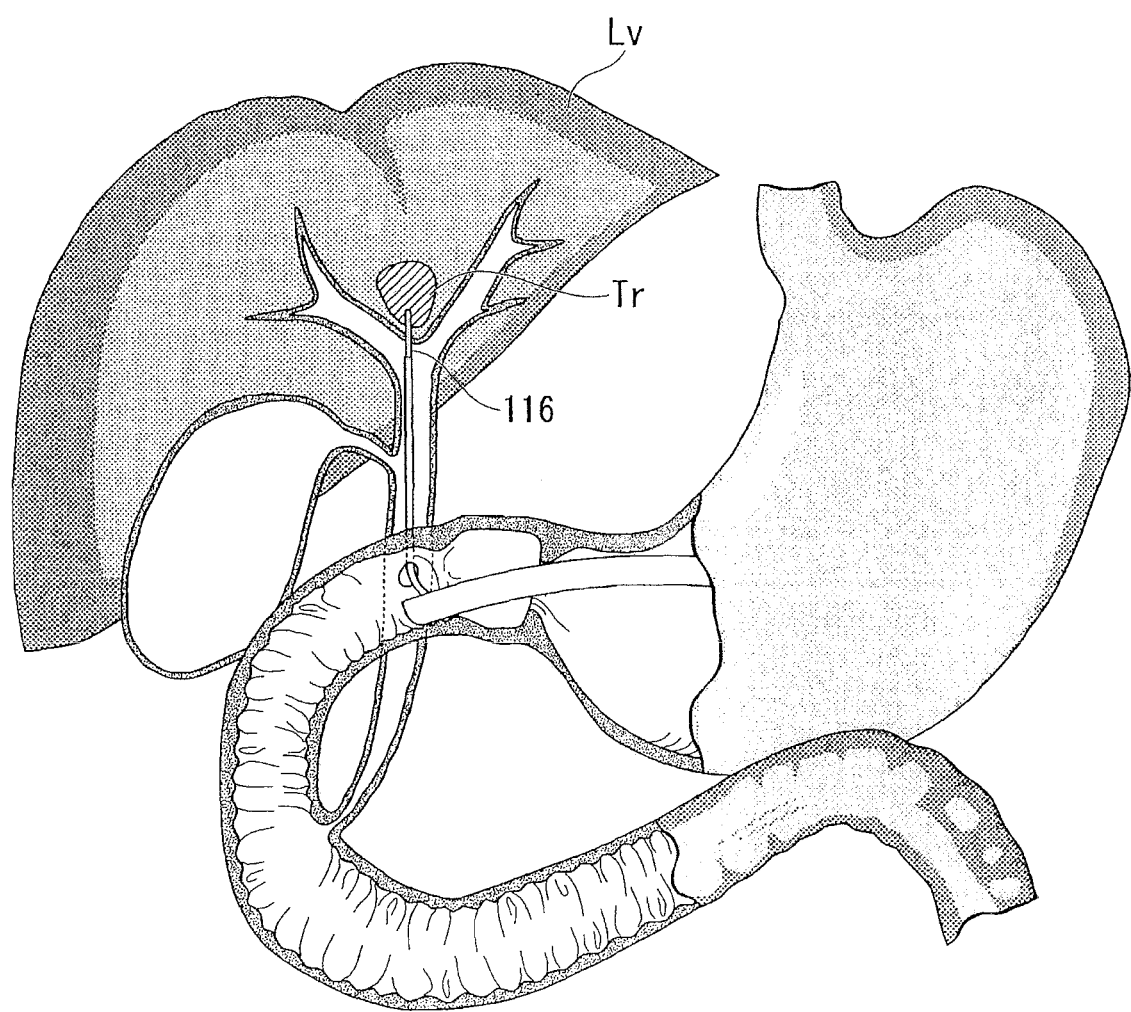
FIG. 22 shows another example of a treatment method of the same embodiment.
Figure 23:
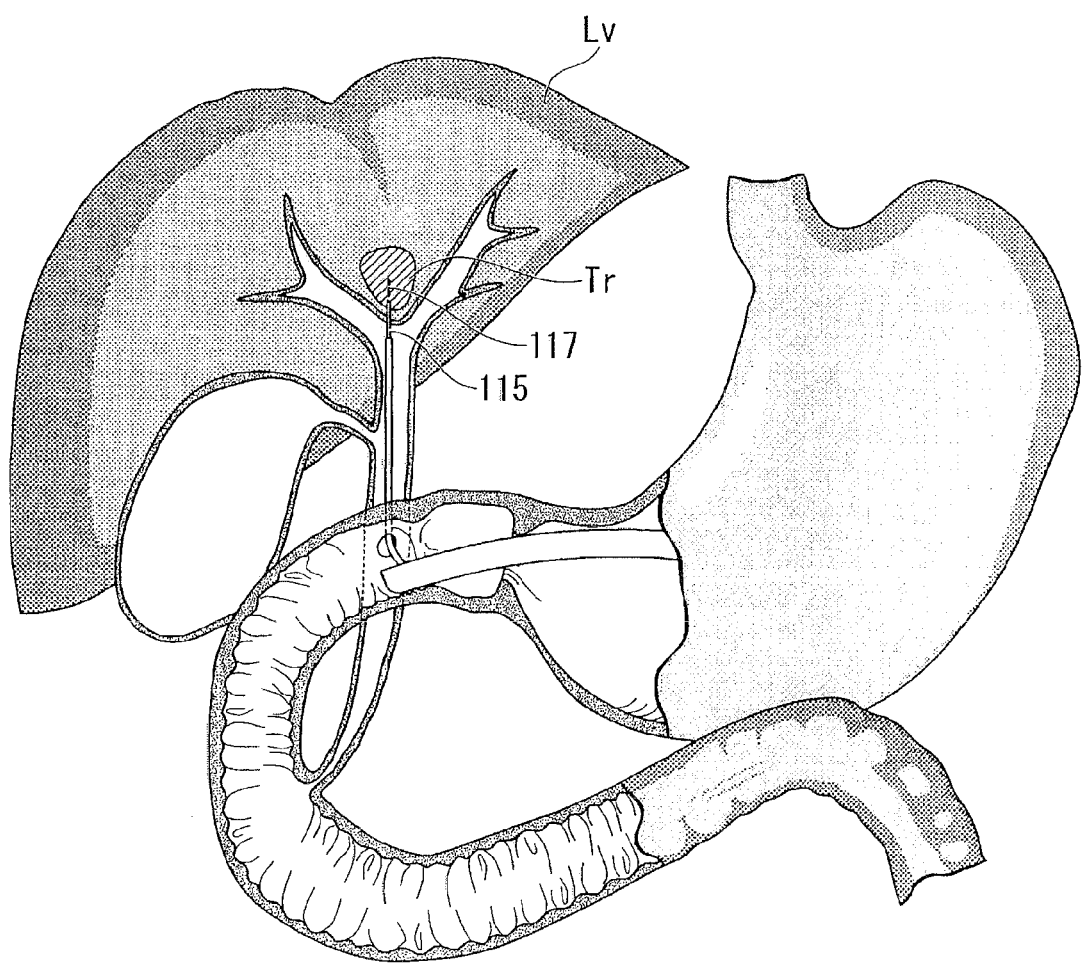
FIG. 23 shows still another example of a treatment method of the same embodiment.

Next is a description of a treatment method of a fourth embodiment according to the present invention. FIG. 21 to FIG. 23 all show one example of a manipulation performed after approaching a hepatic parenchyma, which is a treatment method of the present embodiment.

FIG. 21 shows a state in which a treatment device with a needle 115 at its tip end is approached to a tumor Tr in a liver Lv so as to reversely move through a bile duct. The user piercingly inserts the needle 115 into the tumor Tr and administers various types of drug solution such as an antitumor agent and pure ethanol while checking the position of the tumor Tr with a CT apparatus or the like.

It is possible to perform such a manipulation far more easily than the conventional approach by the treatment device from a duodenal papilla Dp.

The treatment method on the target tissue in the hepatic parenchyma according to the present embodiment is not limited to the above example. For example, as in a modification shown in FIG. 22, a treatment device with a heat probe 116 at its tip end may be inserted to approach a tumor Tr. Then, the heat probe 116 may be piercingly inserted into a tumor Tr to cauterize the tumor Tr with high-frequency current or the like.

Furthermore, as in a modification shown in FIG. 23, after piercing insertion of the needle 115, an X-ray untransmissive marker 117 may be injected into a tumor Tr to be left there, and a radiation treatment may be performed with the marker 117 as a target. Furthermore, by leaving a radiation source made of a radioactive isotope instead of leaving the marker 117, it is possible to perform a so-called brachytherapy.

Figure 24A:
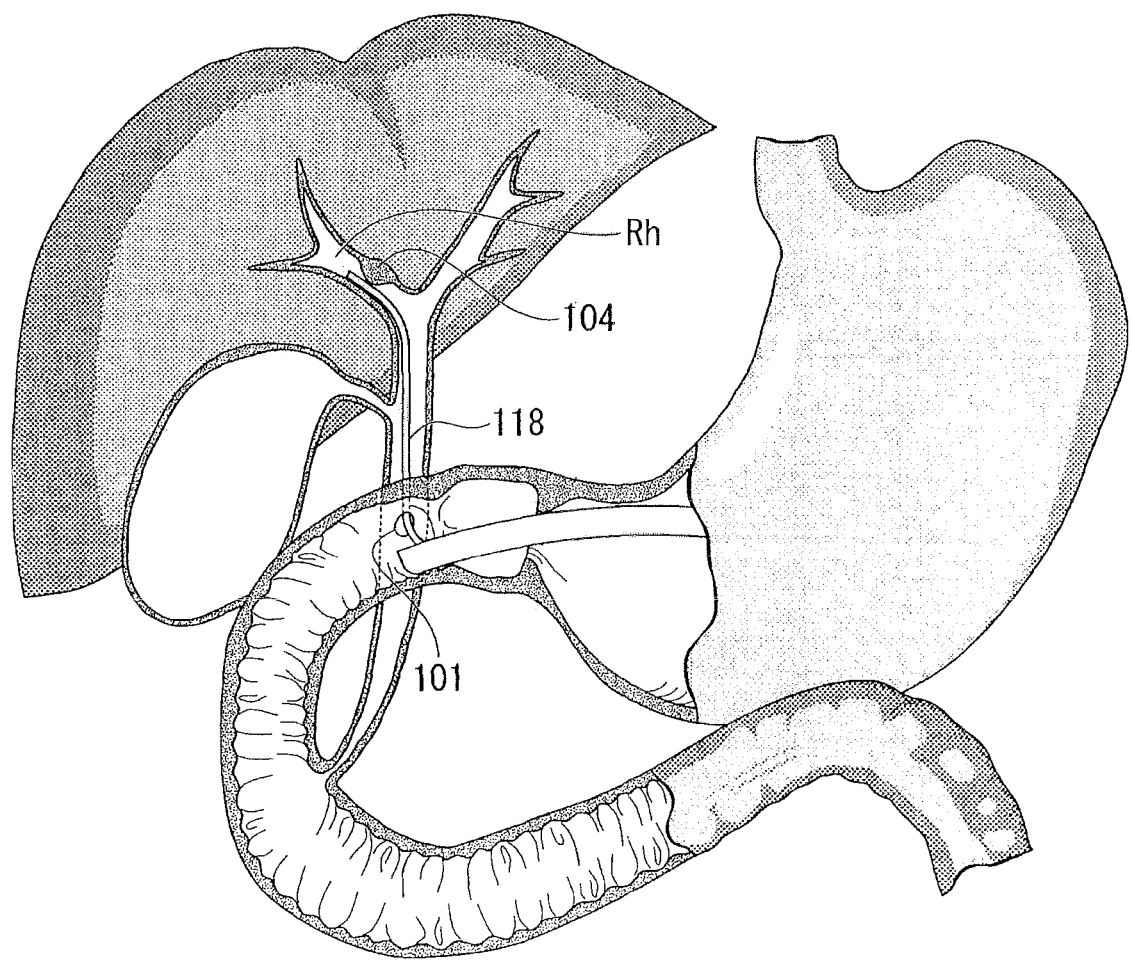
FIG. 24A to FIG. 24C show one example of a treatment method of a fifth embodiment according to the present invention.
Figure 24B:
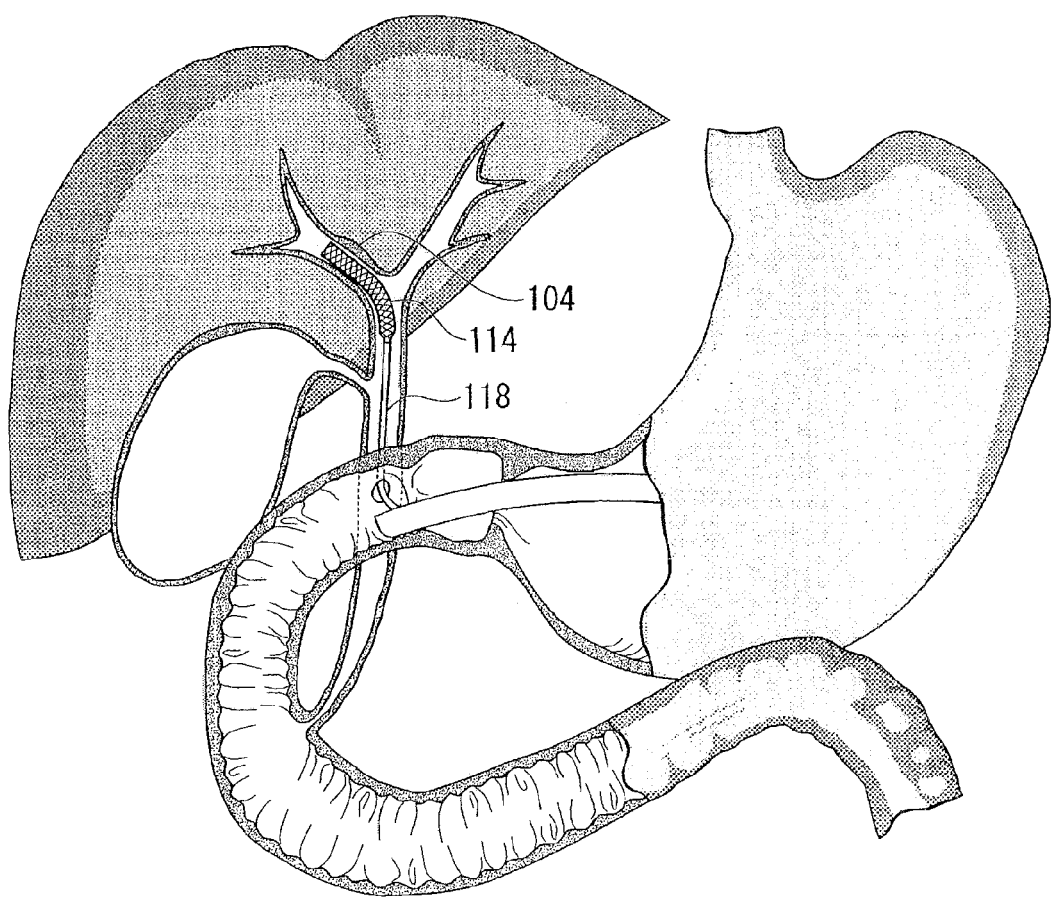
Figure 24C:
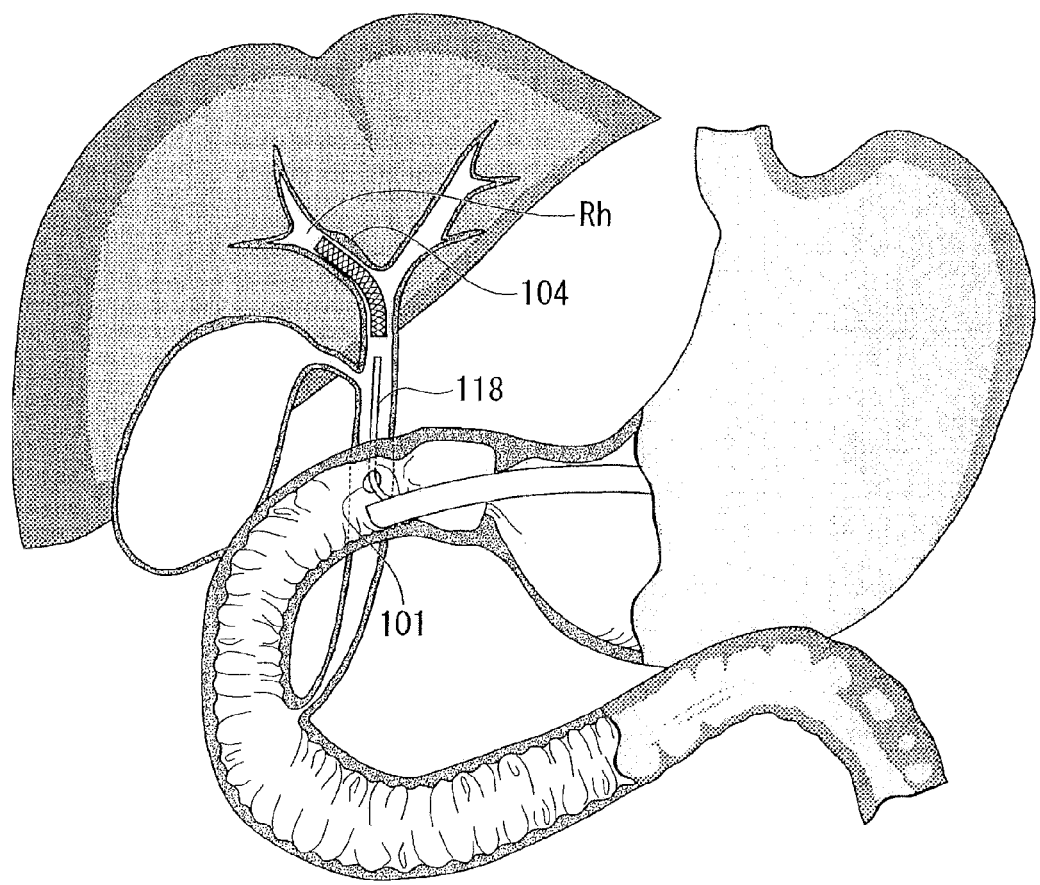

Next is a description of a treatment method of a fifth embodiment according to the present invention. FIG. 24A to FIG. 24C all show one example of manipulation on an intrahepatic bile duct, which is a treatment method of the present embodiment.

For example, as shown in FIG. 24A, in the case where a right hepatic duct Rh has a constriction 104 due to a tumor or the like and hence bile is retained in a liver, the user moves forward a catheter 118 containing a metallic stent 114 in its lumen from a fistula 101 and causes it to pass through the constriction 104. Then, as shown in FIG. 24B and FIG. 24C, while moving back the catheter 118, the user uses a pusher or the like (not shown in the figures) inserted through the catheter 118 to push the metallic stent 114 out of the catheter 118. On completion of leaving the metallic stent 114, the constriction 104 is expanded to allow the bile to be favorably discharged to the bile duct. At this time, drainage by use of a tube or the like may be performed as required.

It is possible to perform the treatment method on an intrahepatic bile duct according to the present embodiment also far more easily and more safely than the conventional approach though a duodenal papilla.

Figure 25:
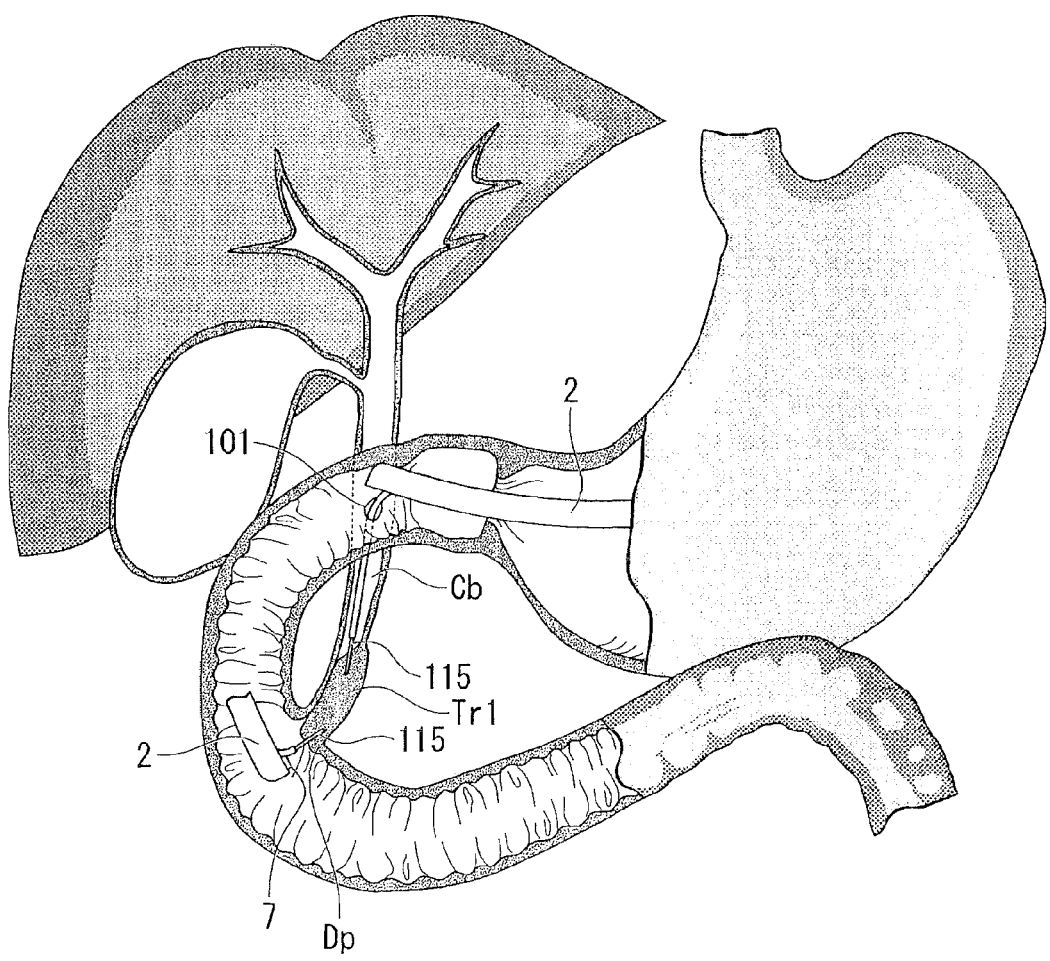
FIG. 25 shows one example of a treatment method of a sixth embodiment according to the present invention.

Next is a description of a treatment method of a sixth embodiment according to the present invention. FIG. 25 shows one example of a manipulation of approaching a downstream side of a bile duct from a fistula, which is a treatment method of the present embodiment.

In FIG. 25, as one example of a lesion on a downstream side of a bile duct, there is formed a tumor Tr1 extending from the vicinity of a duodenal papilla Dp along a common bile duct Cb, the tumor Tr1 having a larger dimension in the longitudinal direction. In the case of such a tumor, even if a drug solution is injected into the vicinity of one end portion of the tumor in the longitudinal direction, the drug solution does not cover the whole tumor. Therefore, it is difficult in general to obtain a sufficient effect.

Therefore, the user first moves a treatment device from a fistula 101 through a common bile duct Cb to an end portion on an upstream side of a tumor Tr1, and piercingly inserts a needle 115 into the tumor Tr1 to inject a drug solution. After that, the user pulls the treatment device out of the fistula 101, and moves a tip end of an endoscope 2 to a duodenal papilla Dp. The user then uses an elevator 7 or the like to piercingly insert the needle 115 into an end portion on a downstream side of the tumor Tr1 and injects the drug solution. Note that the order of injecting a drug solution may be appropriately changed according to the shape or the like of the tumor Tr.

As a result, it is possible to administer a drug solution to the whole tumor Tr1. Therefore, a higher curative effect can be expected.

Incidentally, the fistula formed in the treatment method of the present invention is a communication path that does not exist in a living body by nature. Therefore, if it is left as it is for a given period of time, it is closed by itself through self repair of tissue. However, in the case where a body fluid or the like continuously passes through the fistula for some reason, the fistula is kept patent.

Therefore, in the case of the fistula for communicating the duodenum with the common bile duct in the above respective embodiments, bile is discharged from the fistula during the time when the bile is not allowed to be discharged from the duodenal papilla. Therefore, the fistula is kept patent. Furthermore, it is also possible to control a patency period by artificially obstructing the duodenal papilla. Through control over a patency period, it is possible to keep the fistula patent until the end of the treatment using the fistula as described above, and to close the fistula when the treatment is over.

Hereunder is a description of a treatment device used for such an object, and an obstruction method of a duodenal papilla using the treatment device.

Figure 26:
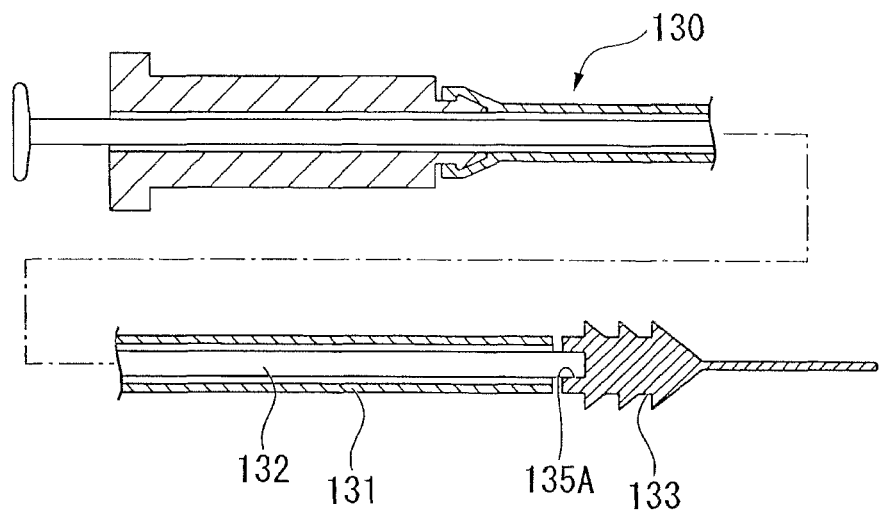
FIG. 26 shows one example of a treatment device for obstructing a duodenal papilla.

FIG. 26 shows the construction of a treatment device 130 for obstructing a duodenal papilla. The treatment device 130 includes: a sheath 131 with flexibility; a pusher 132 that is inserted through the sheath 131; and a plug 133 for obstructing a duodenal papilla that is detachably attached to a tip end of the pusher 132.

Figure 27:
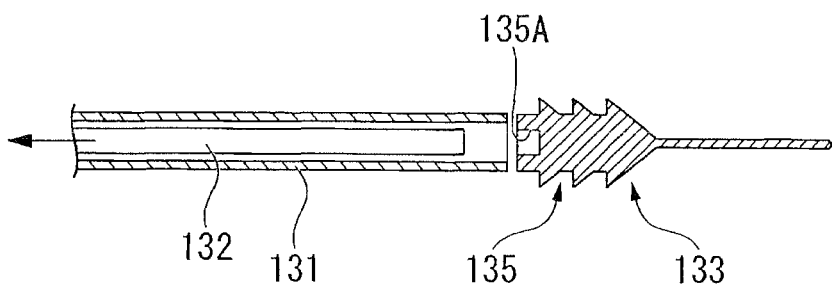
FIG. 27 shows an operation of the treatment device in use.
Figure 28:
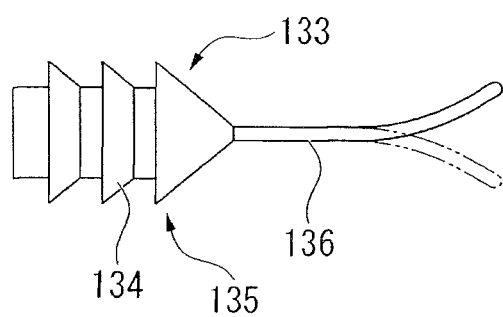
FIG. 28 shows a plug of the treatment device.

As shown in FIG. 27 and FIG. 28, the plug 133 includes: a main unit 135 with flanges 134; and a guide member 136 that is attached to a tip end of the main unit 135. The flange 134 is formed in a tapered shape so as to have a smaller diameter in the direction closer to the tip end. As the guide member 136, a guide wire or the like can be favorably adopted.

The pusher 132 is inserted through the sheath 131 so as to freely advance and retract. A tip end thereof is fit into a recess portion 135A provided in a base end of the main unit 135 of the plug 133. As a result, the pusher 132 and the plug 133 are fixed together by friction. An outer diameter of the main unit 135 is set to be larger than an inner diameter of the sheath 131. Therefore, when the pusher 132 is retracted with respect to the sheath 131, the base end of the plug 133 abuts a tip end of the sheath 131. Furthermore, as shown in FIG. 27, the tip end of the pusher 132 is detached from the recess portion 135A, and hence the plug 133 is separated from the pusher 132.

An obstruction method of a duodenal papilla using the treatment device 130 constructed as above will be described.

Figure 29A:
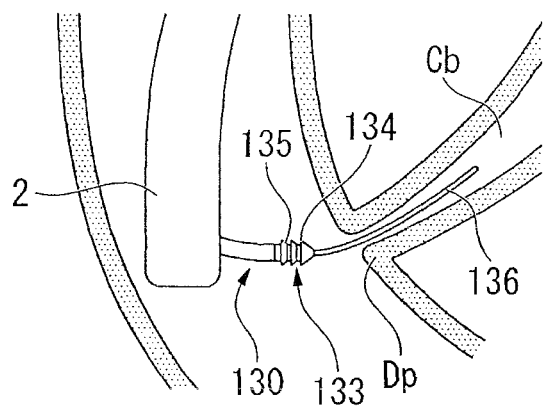
FIG. 29A to FIG. 29C show an operation of the treatment device in use.

First, the user inserts an endoscope 2 as far as the vicinity of a duodenal papilla Dp, and protrudes a treatment device 130 from a tip end thereof while appropriately operating an elevator 7 (not shown in the figure). Then, as shown in FIG. 29A, the user inserts the guide member 136 of the plug 133 into a common bile duct Cb from a duodenal papilla Dp.

Figure 29B:
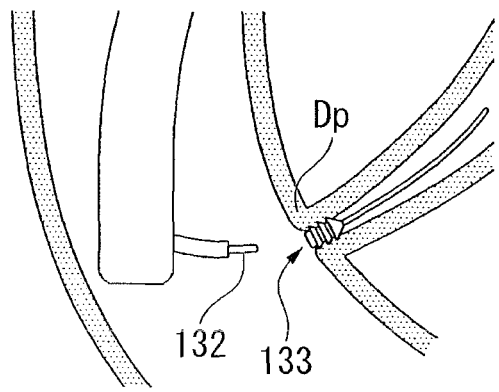

Next, the user moves forward the treatment device 130 to push the main unit 135 of the plug 133 into the common bile duct Cb. After confirming that the flanges 134 of the main unit 135 have been sufficiently engaged with a wall surface of the common bile duct Cb, the user moves back the pusher 132. Then, as shown in FIG. 29B, the plug 133 is separated from the pusher 132, and the duodenal papilla Dp is obstructed by the plug 133.

Figure 29C:
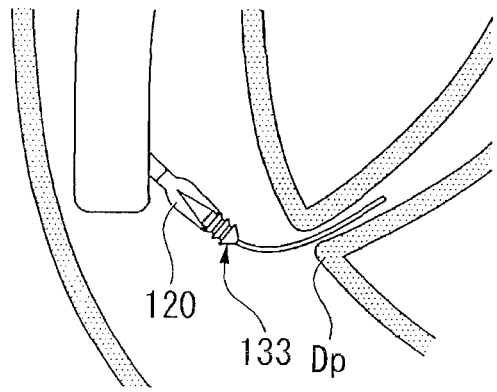

In this state, bile is not discharged from the duodenal papilla Dp. Consequently, the bile is discharged from the fistula formed with the tissue fastening apparatus S1. Therefore, the fistula will not be closed by self repair. At the time when it is not necessary to keep the fistula patent, the user uses grasping forceps 120 or the like to pull the plug 133 out of the duodenal papilla Dp, as shown in FIG. 29C. This allows the bile to be discharged from the duodenal papilla Dp. Therefore, the fistula is closed by self repair.

Figure 30:
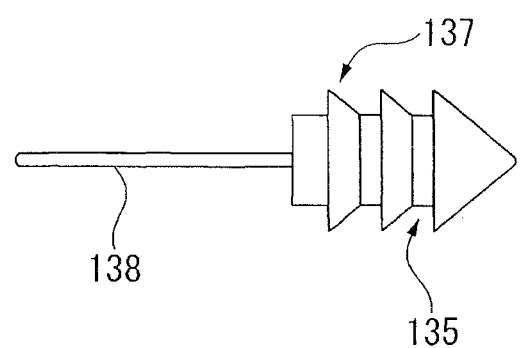
FIG. 30 shows a second example of the plug.

FIG. 30 shows another example of a plug 137. A main unit 135 of the plug 137 is identical to the aforementioned plug 133. However, instead of the guide member 136, a drawer member 138 is attached to a base end of the main unit 135 so as to protrude from a recess portion 135A.

Figure 31:
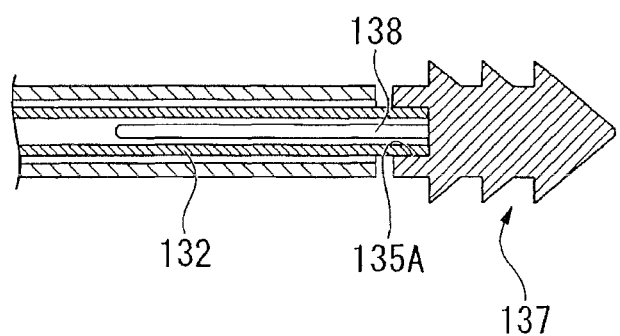
FIG. 31 shows one example of a treatment device that corresponds to the second plug.

Note that as will be described later, the drawer member 138 is not indispensable to the plug 137. However, in the case where the drawer member 138 is provided, a hollow construction of a pusher 132 as shown in FIG. 31 allows the plug 137 to be attached to the pusher 132 with the drawer member 138 contained in a lumen of the pusher 132. Therefore, this is convenient.

Figure 32A:
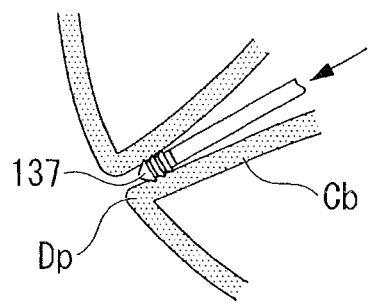
FIG. 32A to FIG. 32C show an operation of the treatment device in use.
Figure 32B:
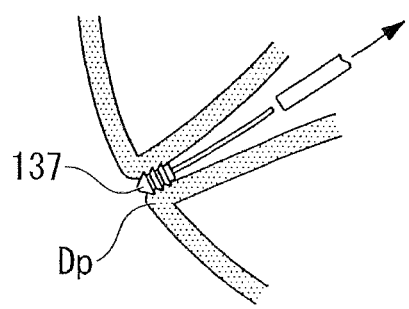

When using the plug 137 to obstruct a duodenal papilla Dp, the user inserts a treatment device 130 from a fistula and moves the treatment device 130 to the vicinity of the duodenal papilla Dp. Then, as shown in FIG. 32A, in substantially the same procedure as described above, the user pushes the plug 137 into the duodenal papilla Dp from a common bile duct Cb side, and moves back the pusher 132 to leave the plug 137, as shown in FIG. 32B.

Figure 32C:
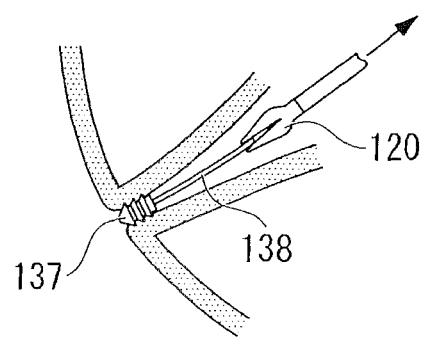

When pulling out the plug 137, the user uses grasping forceps 120 or the like to grasp a drawer member 138, and pulls out the plug 137, as shown in FIG. 32C. Thus, because the plug 137 is provided with the drawer member 138, it is possible to pull out the plug 137 by grasping the drawer member 138. Note that a drawer member is not necessarily indispensable to the plug 137. A construction without a drawer member is permissible.

Furthermore, instead of obstructing a duodenal papilla by using a plug as described above, a duodenal papilla may be completely obstructed by means of cautery or the like to exert control so that a fistula is kept patent as a bile discharge outlet.

Next is a description of a treatment method of a seventh embodiment according to the present invention. The treatment method of the present embodiment is a manipulation of approaching a pancreatic parenchyma from a fistula.

Figure 33:
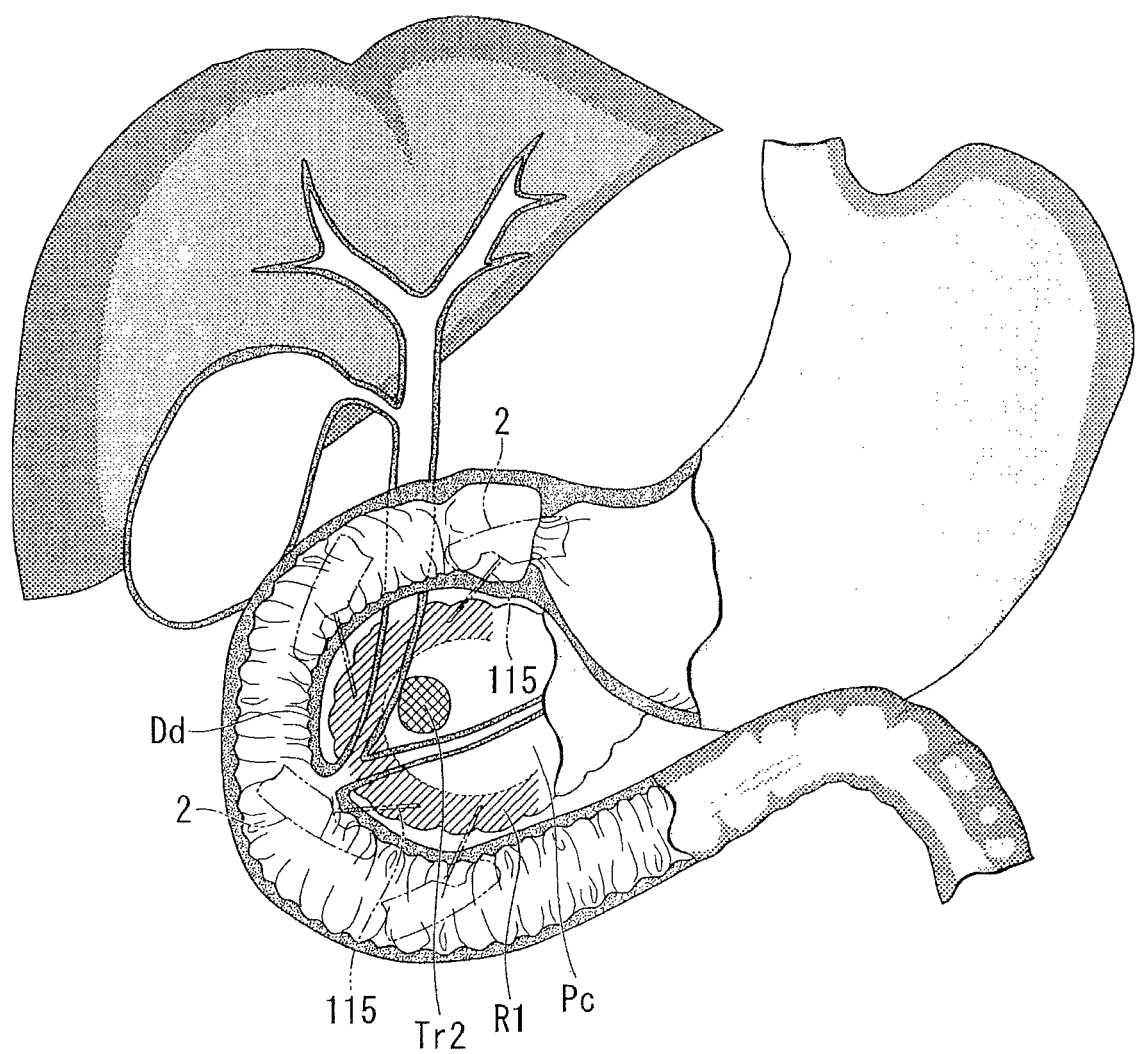
FIG. 33 shows a conventional treatment on a pancreatic parenchyma by use of an endoscope.

FIG. 33 shows a conventional treatment on a pancreatic parenchyma using an endoscope. Conventionally a treatment of piercingly inserting a needle 115 into a pancreas Pc across a wall surface of a duodenum Dd, such as an endoscopic ultrasound-guided fine needle aspiration (EUS-FNA), is performed by use of an endoscope 2. However, in this treatment method, the length of the needle 115 and the angle at which the needle 115 is piercingly inserted are limited. This limits the treatable area to a peripheral region R1 of a pancreas head. Therefore, it is difficult to treat a lesion which lies deeper than that, such as a tumor Tr2.

Figure 34:
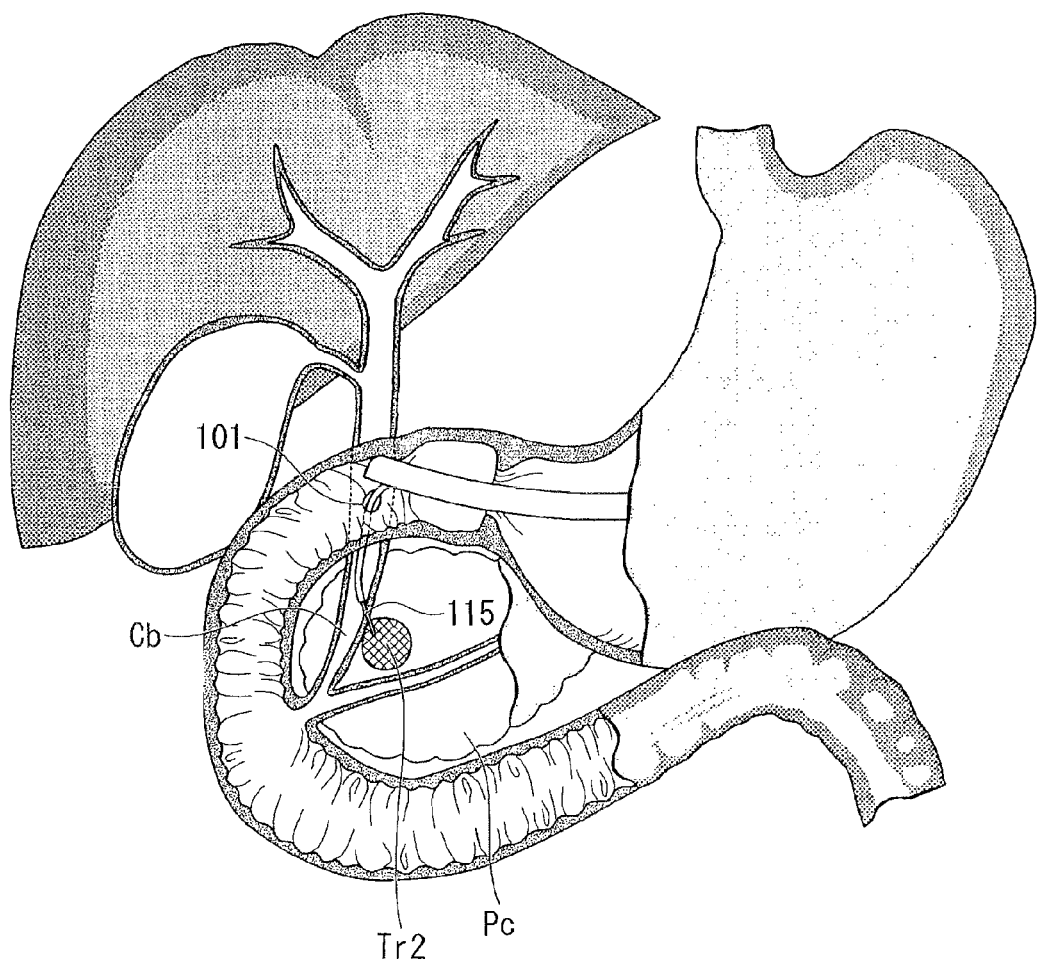
FIG. 34 shows one example of a treatment method of a seventh embodiment according to the present invention.

FIG. 34 shows one example of a treatment method according to the present embodiment. A pancreatic parenchyma is approached from a common bile duct Cb via a fistula 101. Therefore, it is possible to perform a treatment even on a target area such as a tumor Tr2 which lies in a deep portion.

Next is a description of an eighth embodiment of a treatment method according to the present invention. In the treatment method of the present embodiment, a fistula is formed so as to allow a pancreas to communicate with a stomach.

Figure 35:
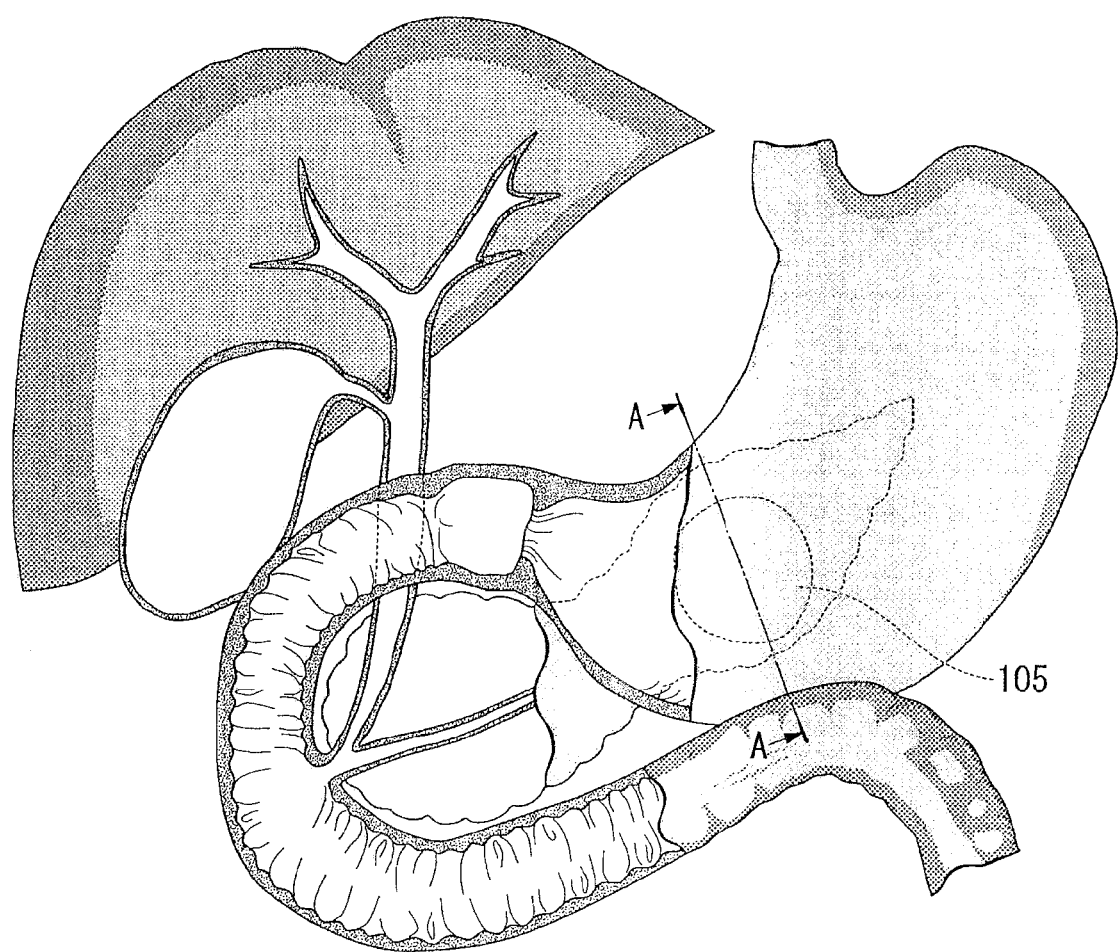
FIG. 35 shows one example of a pancreatic cyst.

FIG. 35 shows a pancreatic cyst, which is one example of an applicable disorder of the treatment method according to the present embodiment. A pancreatic cyst is a cyst formed in a pancreatic parenchyma. The following description of the treatment method according to the present embodiment will be given, taking the case where a cyst 105 is formed in an area shown in FIG. 35 as an example.

FIG. 36 to FIG. 39 all show a procedure of the treatment method according to the present embodiment, on a cross section taken along the line A-A of FIG. 35.

Figure 36:
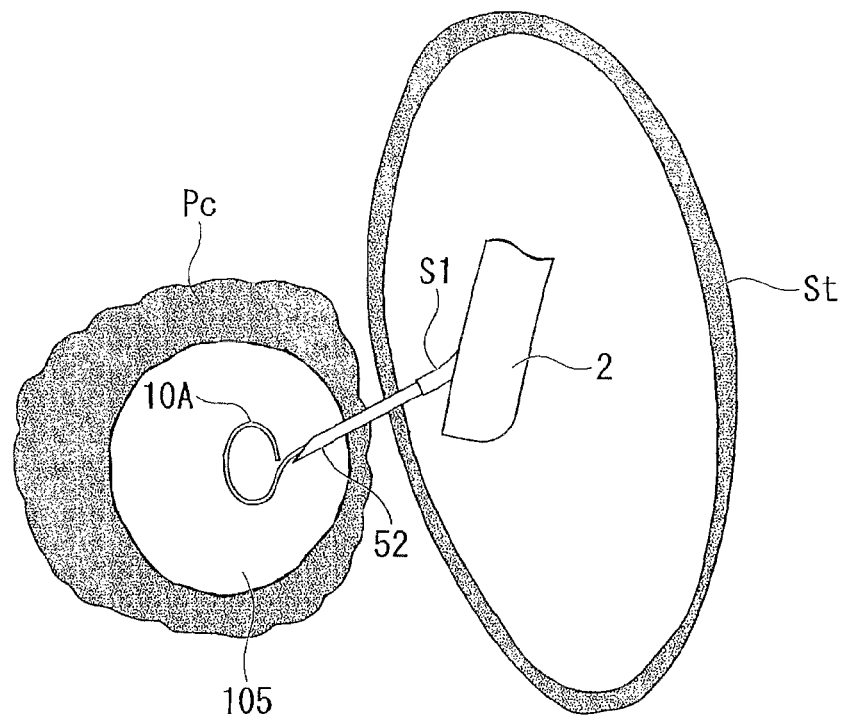
FIG. 36 to FIG. 39 show one example of a treatment method of an eighth embodiment according to the present invention.
Figure 37:
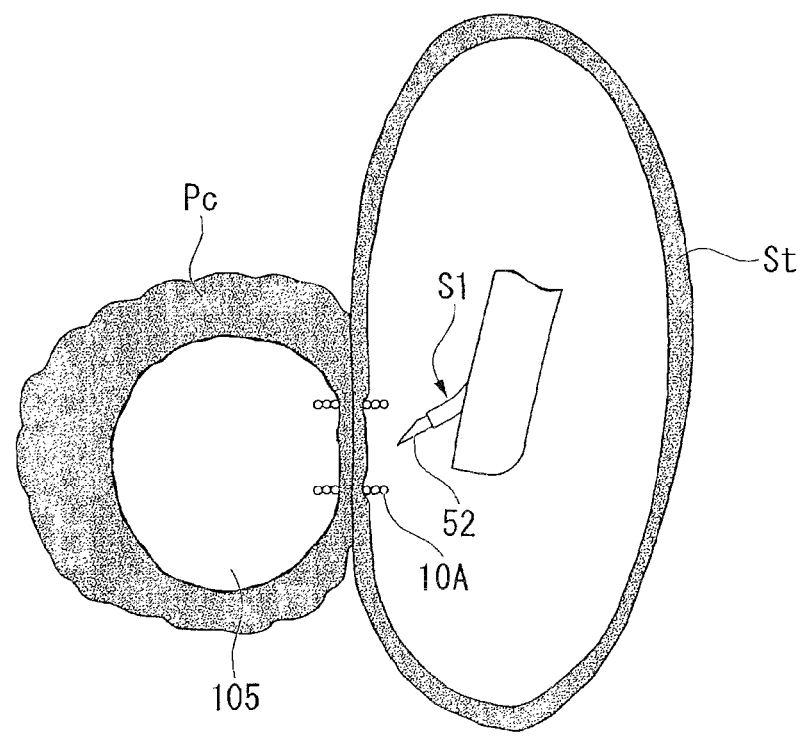

First, the user inserts an endoscope 2 into a stomach St, and protrudes a tissue fastening apparatus S1 from a tip end thereof. Then, while checking the position of a cyst 105 by the ultrasound imaging or the like, the user piercingly inserts a piercing device 52 into a stomach wall, and protrudes a tip end of the piercing device 52 into an interior of the cyst 105 through the stomach wall and a pancreas Pc, as shown in FIG. 36. Furthermore, the user pushes out a fastener 10A from the piercing device 52, and closely fixes the pancreas Pc and the stomach St together as shown in FIG. 37, in the manner as described above. At this time, an internal wall of the cyst 105 is far harder than a normal pancreatic parenchyma due to a fibril formation or the like. Therefore, it is possible to favorably fix both organs together by the fastener 10A.

Figure 38:
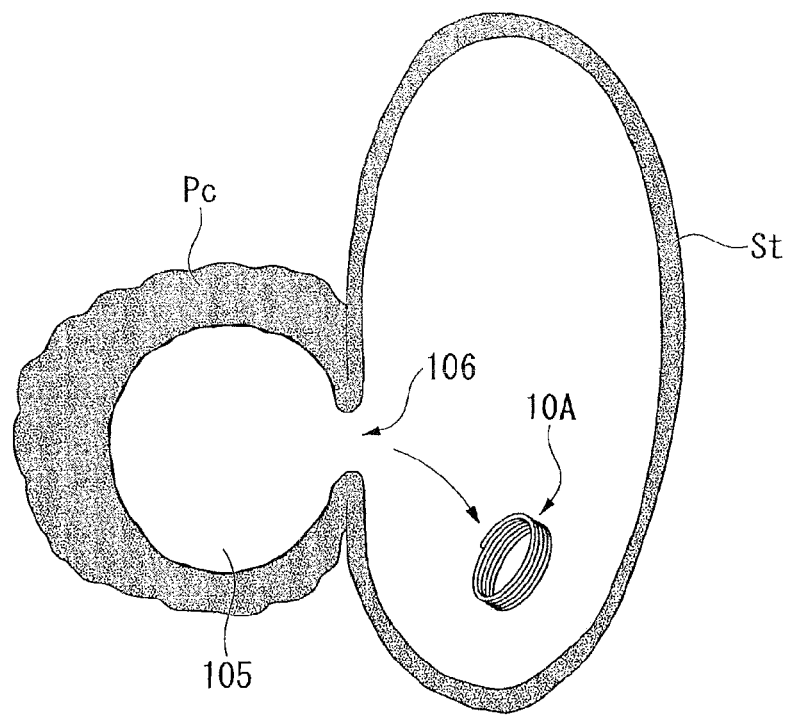
Figure 39:
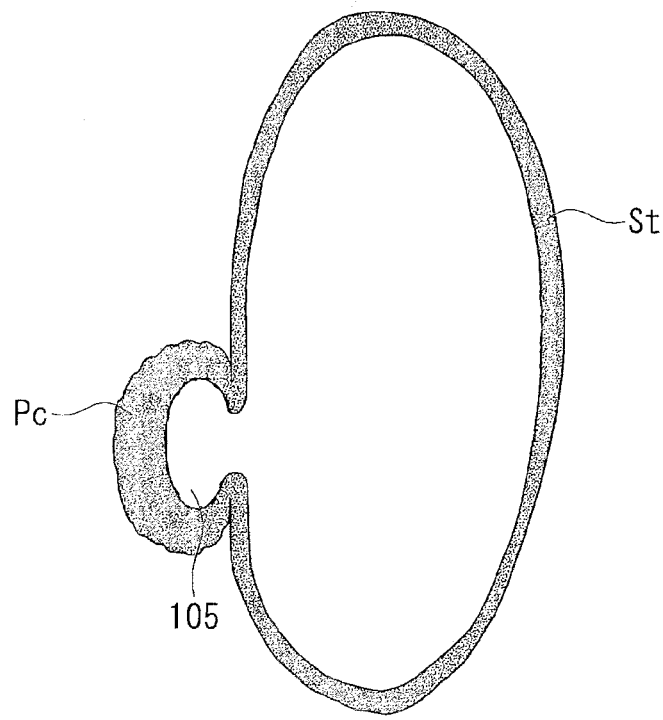

In the course of time, by the necrosis of the tissues around the through-hole, the fastener 10A falls off as shown in FIG. 38, and thereby a fistula 106 for communicating the stomach St with the pancreas Pc is formed. Then, liquid in the cyst 105 is discharged into the stomach St through the fistula 106. As a result, as shown in FIG. 39, the cyst 105 is reduced in size, and cured.

Typically, in a drainage treatment on a pancreatic cyst, the area where the stomach and the pancreas are adhered is utilized to approach the cyst from the stomach, to thereby prevent the liquid in the cyst from leaking into the abdominal cavity. According to the treatment method of the present embodiment, a fistula can be formed even in an area where the stomach and the pancreas are not adhered. This broadens the treatable area, and allows easier manipulation on a cyst.

Figure 40:
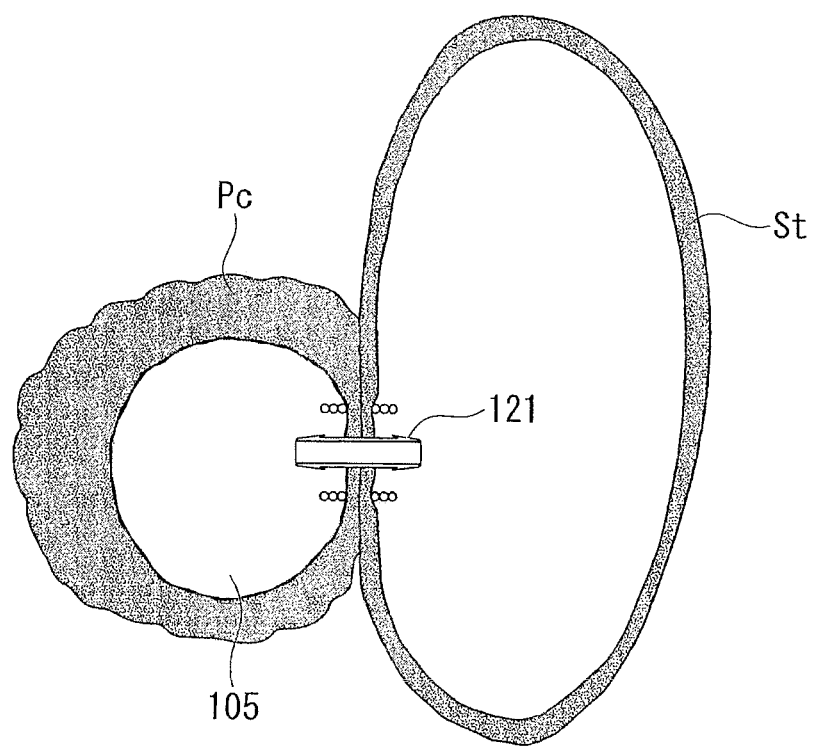
FIG. 40 shows a modification of the treatment method of the embodiment.

In the curing of the pancreatic cyst as described above, a plastic stent 121 or the like may be used to communicate a pancreas Pc with a stomach St, as in a modification shown in FIG. 40.

Next is a description of a treatment method of a ninth embodiment according to the present embodiment. In the treatment method of the present embodiment, a fistula is used to form a bypass between gastrointestinal tracts.

Figure 41:
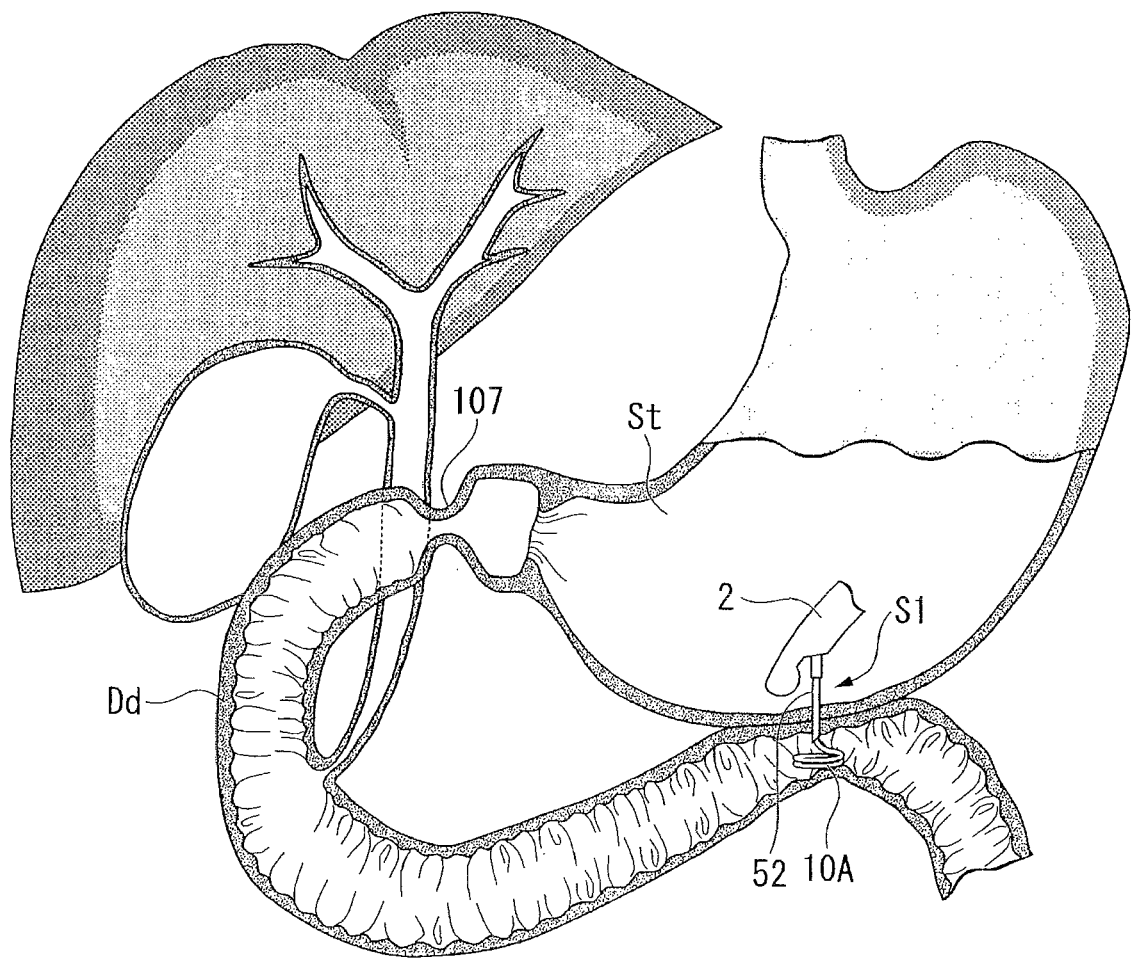
FIG. 41 to FIG. 43 show one example of a treatment method of a ninth embodiment according to the present invention.
Figure 42:
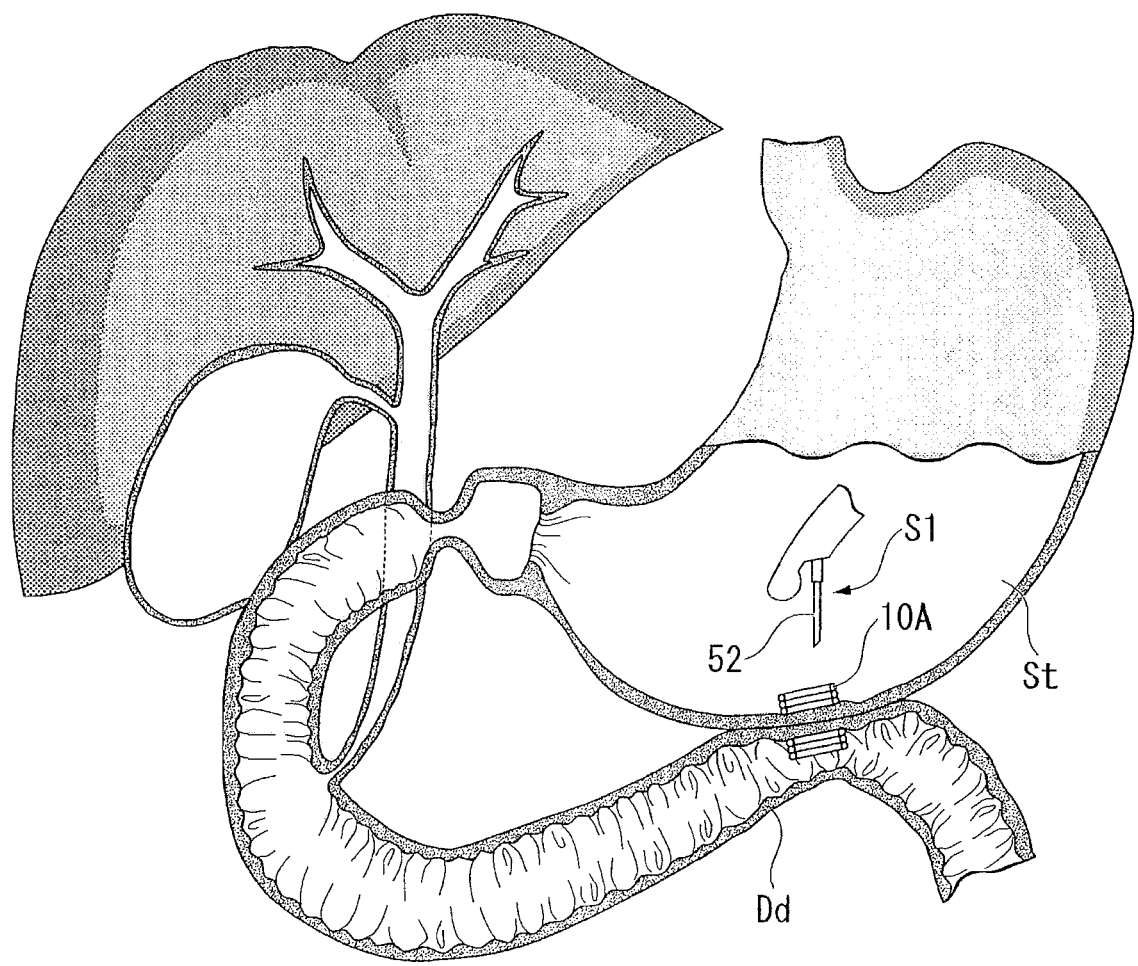

As one example of a target of the treatment method according to the present embodiment, the case where a duodenum Dd has a severe constriction 107 can be listed, as shown in FIG. 41. In such a case, the user inserts an endoscope 2 into a stomach St, penetrates a stomach wall and a duodenum wall with a piercing device 52 of a tissue fastening apparatus S1, and pushes out the fastener 10A from the piercing device 52. Then, as shown in FIG. 42, the user closely fixes the stomach St and the duodenum Dd together with the fastener 10A.

Figure 43:
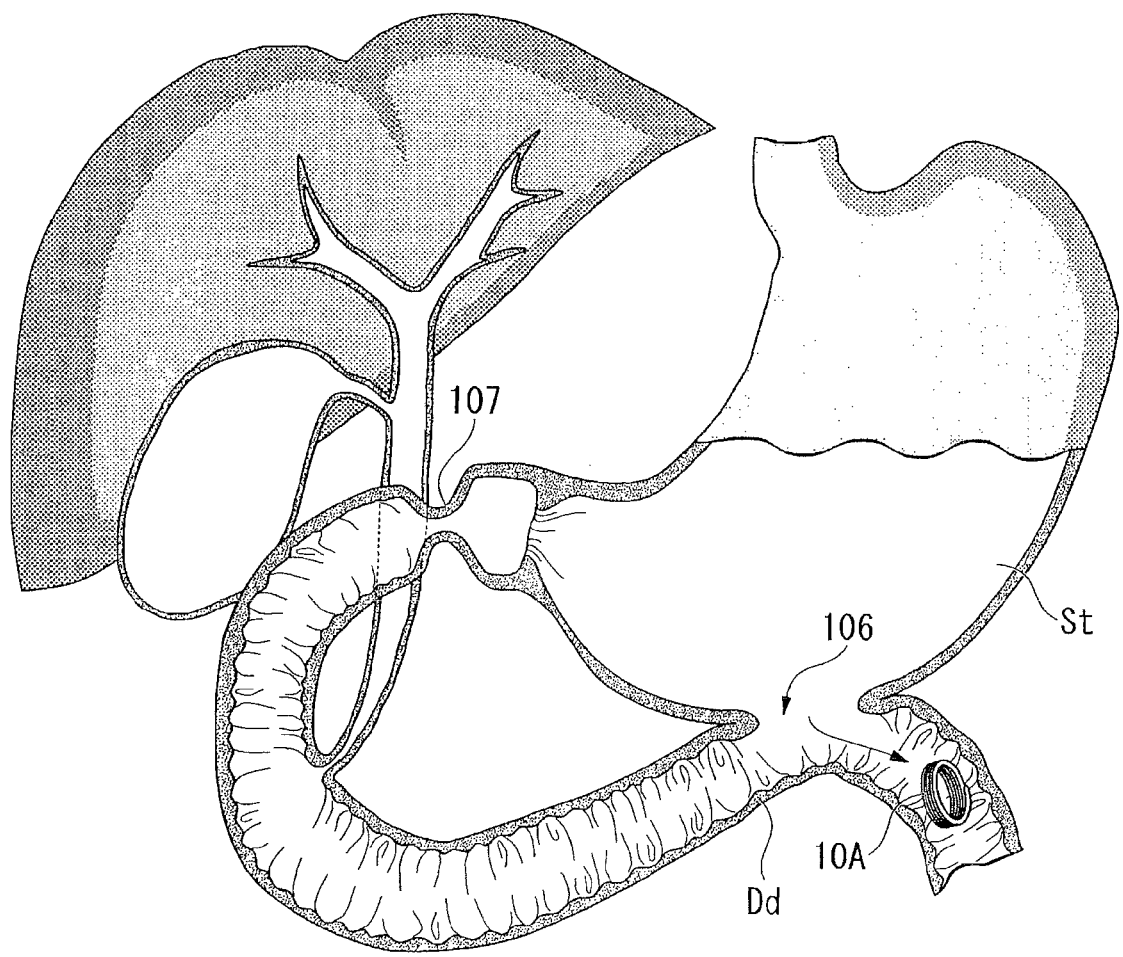

Later, as shown in FIG. 43, the fastener 10A falls off to form a fistula 106 for communicating the stomach St with the duodenum Dd. Thereby, a bypass route that bypasses the constriction 107 is finished.

As for a gastrointestinal tract anastomosis bypass as described above, solid food and the like may pass through it. Therefore, there are cases where a fistula with a diameter larger than that of the aforementioned fistula 101 for communicating the common bile duct Cb with the duodenum Dd is formed. Hereunder is a description of one example of a fistula formation method in such cases.

Figure 44:
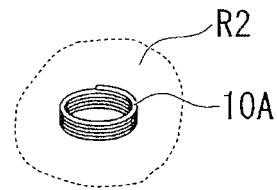
FIG. 44 is a diagram that explains an adhered region.

As has been described above, in an area where the fastener 10A is left, there is formed an adhesion region R2 where the first tissue and the second tissue in close contact are adhered is formed in a given range outside the loop of fastener 10A, as shown in FIG. 44.

Figure 45A:
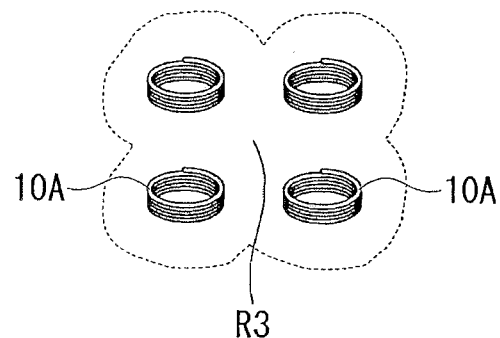
FIG. 45A to FIG. 45C are diagrams that explain a procedure of forming a fistula with a larger diameter.

Therefore, to form a larger fistula, the user places a plurality of fasteners 10A so that their adhesion regions R2 overlap. As a result, as shown in FIG. 45A, it is possible to obtain a larger adhesion region R3.

Figure 45B:
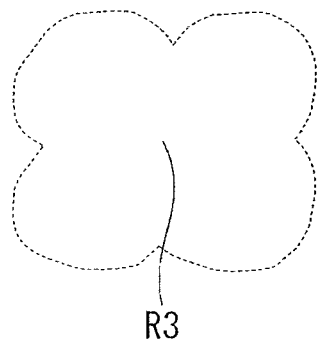
Figure 45C:
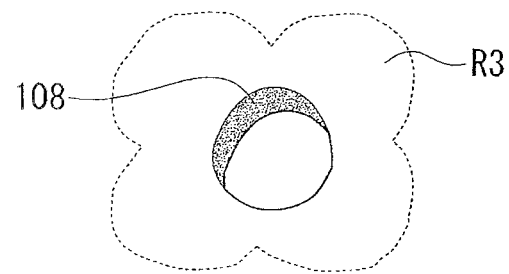

After all the fasteners 10A have fallen off and the through-holes have been filled by self repair in this adhesion region R3 as shown in FIG. 45B, the user bores a hole with a larger diameter in the region R3 to form a fistula 108 as shown in FIG. 45C. It is preferable that as a treatment device for boring a hole, an electrosurgical knife or the like be used from the viewpoint of preventing bleeding.

Figure 46:
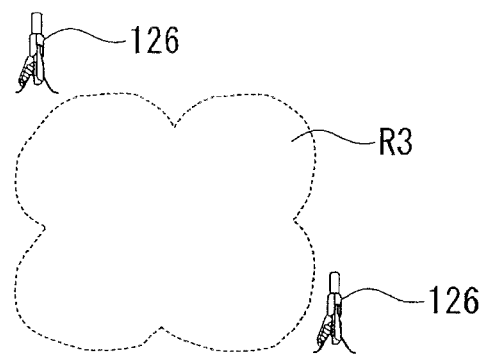
FIG. 46 is a diagram that explains a modification of the procedure.

When the aforementioned hole is formed, the fistula may be formed by exsecting tissue so as to join the through-holes after the fall-off of the fastener 10A, without waiting for the through-holes to be filled. Furthermore, it is difficult to distinguish the adhesion region R3 from unadhered normal tissue in appearance. Therefore, after the placement of the fasteners 10A, markers 126 may be left at positions which are expected to be outer edges of the adhesion region R3, as shown in FIG. 46, so as to be used as guides for forming a fistula.

According to the treatment method of the present embodiment, it is possible to easily form a gastrointestinal tract anastomosis bypass without opening the abdomen, by use of the fasteners 10A.

Figure 47:
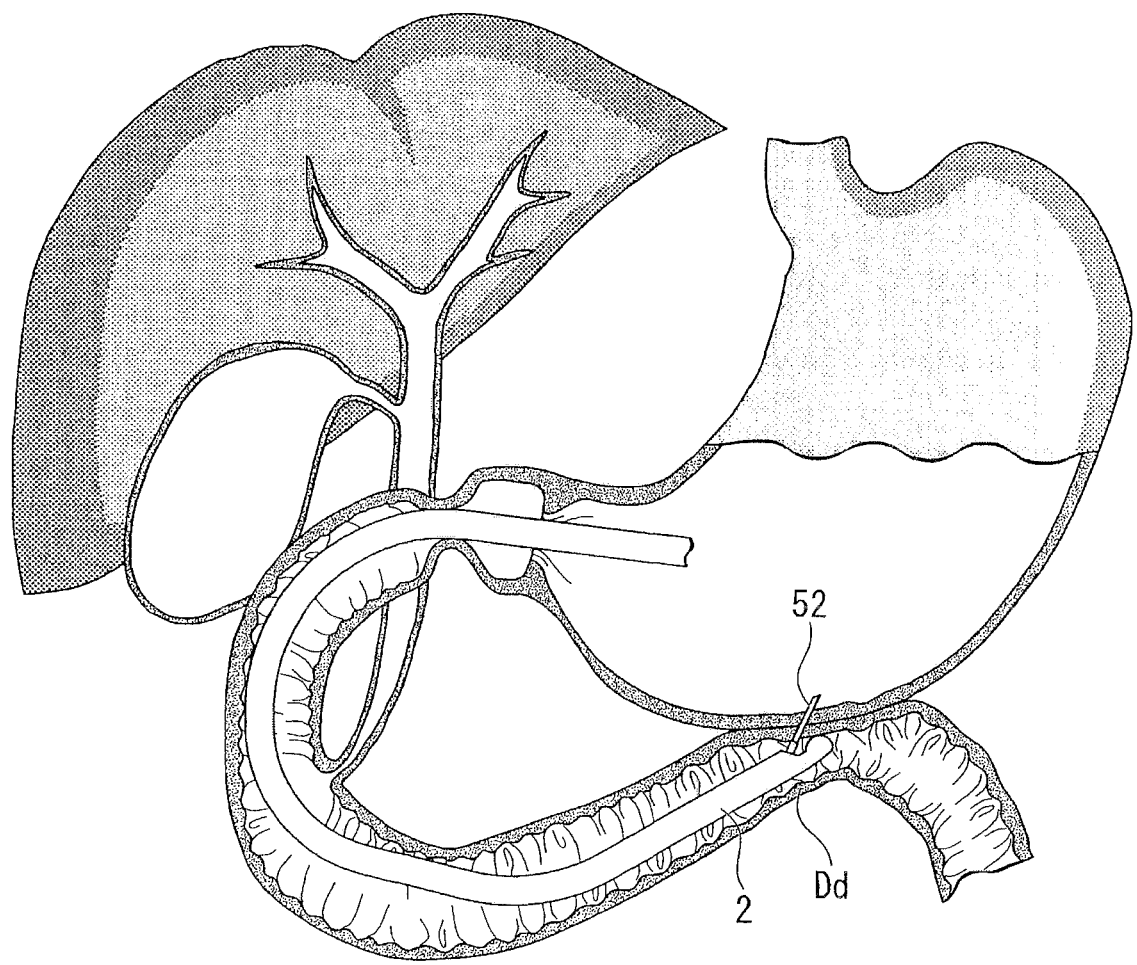
FIG. 47 shows a modification of the treatment method of the embodiment.

In the aforementioned treatment method, the example of piercingly inserting the piercing device 52 from the stomach St side has been described. However, instead of this, as in a modification shown in FIG. 47, the piercing device 52 may be piercingly inserted from the duodenum Dd side to place the fastener 10A. In piercing insertion, the tip end of the piercing device 52 cannot be checked with the endoscope. Therefore, it is safer to piercingly insert the piercing device 52 toward the stomach, which is larger.

While preferred embodiments of the invention have been described and illustrated above, it should be understood that these are exemplary of the invention and are not to be considered as limiting. Additions, omissions, substitutions, and other modifications can be made without departing from the spirit or scope of the present invention.

Figure 48:
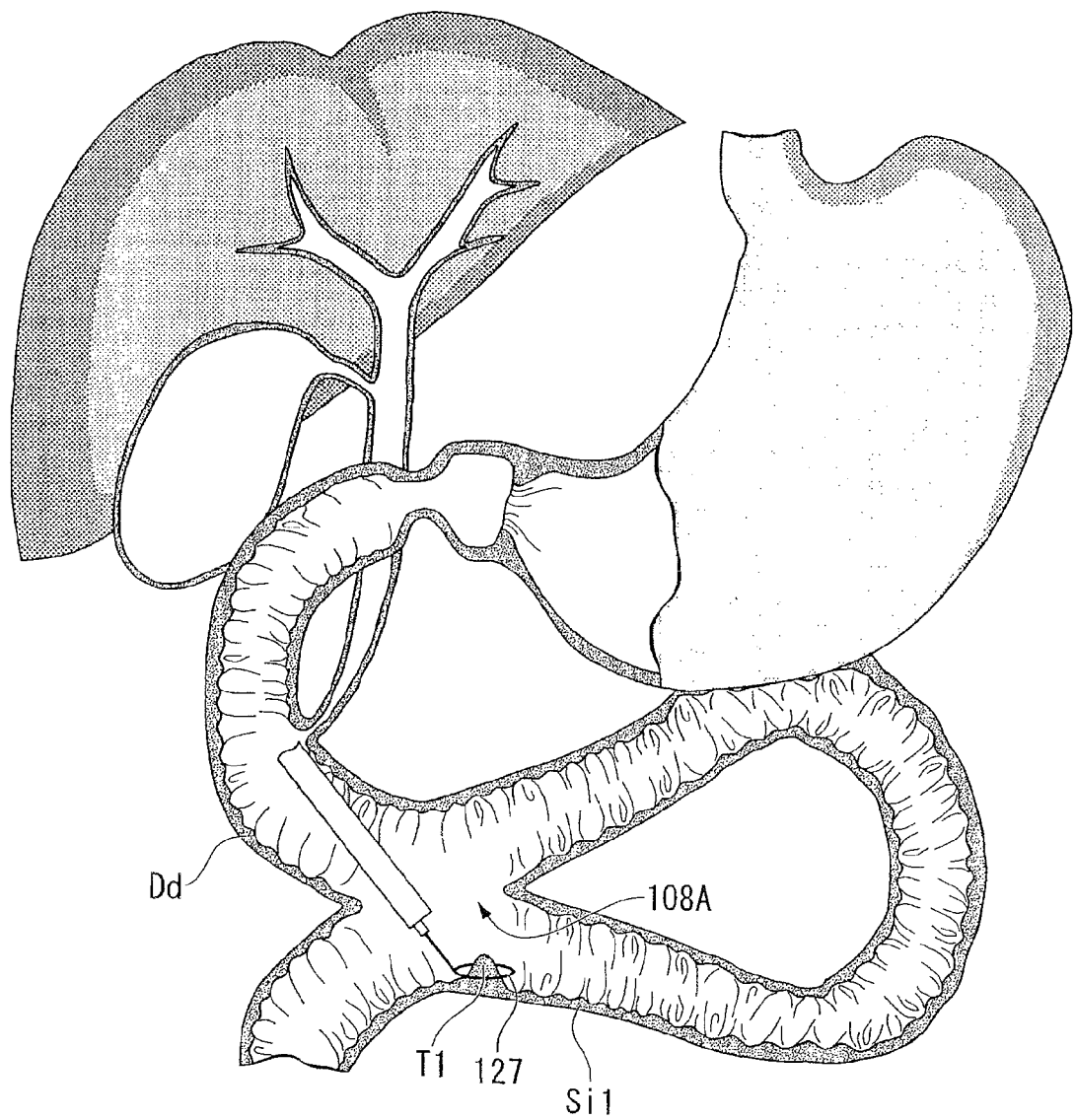
FIG. 48 shows a modification of a treatment method of the present invention.

For example, as in a modification shown in FIG. 48, a fistula 108A may be formed so as to communicate a duodenum Dd with a jejunum Si1, and a target tissue T1 such as a polyp and a tumor in the jejunum Si1 may be approached with various equipment to thereby perform a cure, a checkup, and the like.

Figure 49:
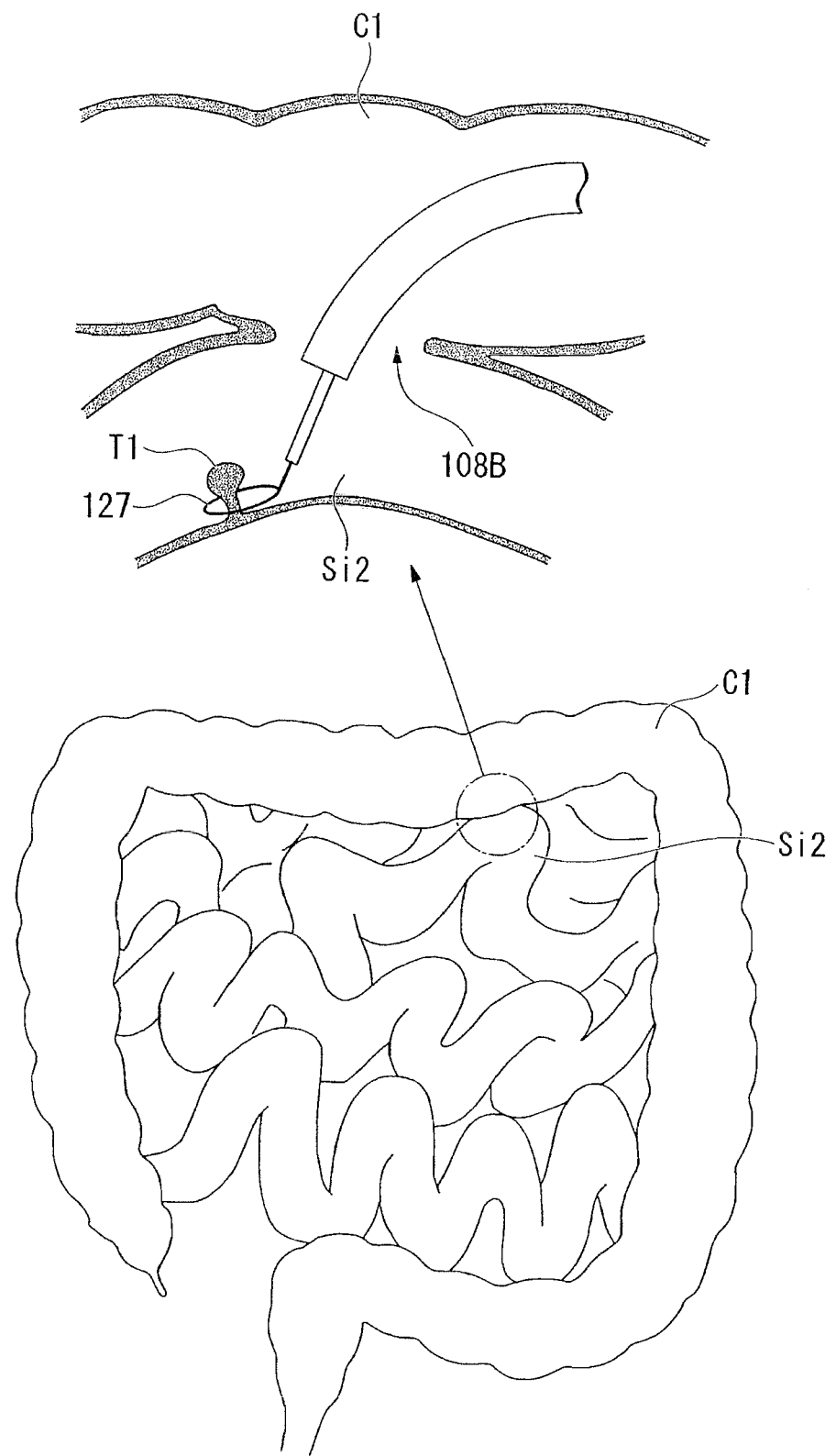
FIG. 49 shows a modification of a treatment method of the present invention.

Furthermore, as in a modification shown in FIG. 49, a fistula 108B may be formed so as to communicate a large intestine C1 with an ileum Si2, and a target tissue T1 such as a polyp and a tumor in the ileum Si2 may be approached with various equipment to thereby perform a cure, a checkup, and the like. In this case, an endoscope 2 is inserted from an anus. As a fistula formation portion, any of an ascending colon, a transverse colon, a descending colon, and a sigmoid colon is permissible.

Small intestinal regions such as a jejunum and an ileum are long, and heavily winding. Therefore, it is typically very difficult to move forward an endoscope, treatment device, or the like to perform a cure or the like. However, according to the treatment methods of the aforementioned modifications, formation of a fistula allows an endoscope to easily move forward into a region in a small intestine to perform a treatment, if the region is in the vicinity of a duodenum or a large intestine.

Furthermore, as a treatment device for use in a treatment, various treatment devices including a snare wire 127 shown in FIG. 48 and FIG. 49, and the like may be used in addition to ones described above.

Other than these, the invention is not to be considered as limited by the foregoing description and is only limited by the scope of the appended claims.

What is claimed is:

1. A treatment method on tissues in a body cavity, the treatment method comprising:
    a first step of placing a fastener comprising a plurality of loops formed in a coiled shape, wherein each of the plurality of loops has the same predetermined diameter, and neighboring loops of the plurality of loops are attached to each other when the fastener is not subjected to external force, wherein the first step comprises the fastener being pushed out from an applicator inserted via a natural orifice of a patient, the fastener compressing both a first body tissue and a second body tissue to be in an ischemic condition, the first body tissue being an outer wall of a horizontal portion of a duodenum, the horizontal portion of the duodenum distal to a stomach and proximal to a downward portion of the duodenum, the second body tissue being an upper portion of a common bile duct, the upper portion of a common bile duct is a distance away from a papilla of the common bile duct; and
    a second step of forming a fistula, having the predetermined diameter of each of the plurality of loops of the fastener, bound by the fastener by ischemic necrosis of the compressed first body tissue and the compressed second body tissue to communicate between the horizontal portion of the duodenum and the upper portion of the common bile duct;
    a third step of introducing a distal portion of an endoscope inserted via a natural orifice of the patient into the duodenum, moving the distal portion of the endoscope to the vicinity of the fistula, protruding a treatment device from the distal portion of the endoscope;
    a fourth step of inserting the treatment device into the common bile duct through the fistula, and performing a treatment by the treatment device in the common bile duct.

2. The treatment method according to claim 1, wherein in the third step, the treatment device is introduced into a gallbladder via the biliary tract.

3. The treatment method according to claim 1, wherein in the third step, the treatment device is introduced into a region of a common hepatic duct or a region, in the biliary tract, closer to a liver than to a common hepatic duct.

4. The treatment method according to claim 1, wherein
    in the third step, the treatment device is introduced into a region, in the biliary tract, closer to a duodenal papilla than to the fistula.

5. The treatment method according to claim 1, wherein the treatment device is a treatment device for injecting a drug solution.

6. The treatment method according to claim 5, wherein the drug solution is a contrast medium.

7. The treatment method according to claim 5, wherein the drug solution is an antitumor agent.

8. The treatment method according to claim 5, wherein the drug solution is ethanol.

9. The treatment method according to claim 1, wherein the treatment device is a treatment device for removing a calculus.

10. The treatment method according to claim 1, wherein the treatment device is a treatment device for crushing a calculus.

11. The treatment method according to claim 1, wherein the treatment device is a treatment device for cautery.

12. The treatment method according to claim 1, wherein the treatment device is a treatment device for leaving a marker.

13. The treatment method according to claim 1, wherein the treatment device is a treatment device for leaving a radiation source.

14. The treatment method according to claim 1, wherein the treatment device is a treatment device for leaving a stent.

15. The treatment method according to claim 1, wherein the treatment device is a guide wire.

16. The treatment method according to claim 1, wherein the fastener is inserted through the first body tissue and second body tissue to maintain the first body tissue and second body tissue in close contact with each other.

17. The treatment method according to claim 16, wherein the fastener forms a coil-like shape on an inner face of the first body tissue and a coil on an inner face of a second body tissue.

* * * * *